United States Patent
Schlessinger et al.

(10) Patent No.: US 11,365,228 B2
(45) Date of Patent: Jun. 21, 2022

(54) MUTANT FGF21 POLYPEPTIDE COMPOSITIONS

(71) Applicant: YALE UNIVERSITY, New Haven, CT (US)

(72) Inventors: Joseph Schlessinger, Woodbridge, CT (US); Sangwon Lee, Branford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/624,895

(22) PCT Filed: Jul. 5, 2018

(86) PCT No.: PCT/US2018/040932
§ 371 (c)(1),
(2) Date: Dec. 19, 2019

(87) PCT Pub. No.: WO2019/010314
PCT Pub. Date: Jan. 10, 2019

(65) Prior Publication Data
US 2020/0131257 A1  Apr. 30, 2020

Related U.S. Application Data

(60) Provisional application No. 62/529,215, filed on Jul. 6, 2017.

(51) Int. Cl.
*C07K 14/50* (2006.01)
*C07K 16/22* (2006.01)

(52) U.S. Cl.
CPC .............. *C07K 14/50* (2013.01); *C07K 16/22* (2013.01); *C07K 2317/76* (2013.01); *C07K 2319/35* (2013.01)

(58) Field of Classification Search
None
See application file for complete search history.

(56) References Cited

U.S. PATENT DOCUMENTS

| | | | |
|---|---|---|---|
| 9,475,856 B2 * | 10/2016 | Mohammadi | G01N 33/74 |
| 2009/0192087 A1 | 7/2009 | Glass et al. | |
| 2009/0298757 A1 * | 12/2009 | Bloom | A61P 3/04 514/1.1 |
| 2011/0135657 A1 | 6/2011 | Hu et al. | |
| 2012/0087920 A1 | 4/2012 | Belouski et al. | |
| 2013/0129725 A1 | 5/2013 | Fachini et al. | |
| 2013/0231277 A1 * | 9/2013 | Mohammadi | G01N 33/74 514/4.8 |
| 2014/0189693 A1 | 7/2014 | Trumbull et al. | |
| 2014/0189893 A1 | 7/2014 | Li et al. | |
| 2015/0368358 A1 | 12/2015 | Desnoyers | |
| 2019/0142963 A1 * | 5/2019 | Dimarchi | A61K 38/03 514/6.9 |

FOREIGN PATENT DOCUMENTS

| | | |
|---|---|---|
| WO | 2009009173 A2 | 1/2009 |
| WO | 2013027191 A1 | 2/2013 |
| WO | 2016088059 A1 | 6/2016 |
| WO | 2016204884 A1 | 12/2016 |
| WO | 2017079768 A1 | 5/2017 |
| WO | 2017205517 A1 | 11/2017 |
| WO | 2018026899 A1 | 2/2018 |

OTHER PUBLICATIONS

Agrawal et al. Mol. Metab. 13: 45-55, 2018.*
Shi et al. Scientific Reports 8: 11045, 2018.*
Lee et al. Nature 553: 501-505, 2018.*
Zhen et al. Biochem. J. 473: 605-614, 2016.*
Bell et al. (Protein Science 22: 1466-1477, 2013).*
Stanislaus et al. Endocrinology 158: 1314-1327, 2017.*
Goetz, et al., "Klotho coreceptors inhibit signaling by paracrine fibroblast growth factor 8 subfamily ligands", Mol Cell Biol. 32(10), May 2012, 1944-1954.
Hernandez, et al., "Pancreatitis is an FGF21-deficient state that is corrected by replacement therapy", Sci Transl Med. 12(525), Jan. 2020, eaay5186.
Hongfei, Ge, et al., "Characterization of a FGF19 variant with Altered Receptor Specificity Revealed a Central Role for FGFR1c in the Regulation of Glucose Metabolism", PLoS One, Mar. 23, 2012, e33603.
Kolumam, Ganesh, et al., "Sustained Brown Fat Simulation and Insulin Sensitization by a Humanized Bispecific Antibody Agonist for Fibroblast Growth Factor Receptor 1/[beta] Klotho Complex", EBioMedicine 2(7), Jul. 1, 2015, 730-743.
Kuzina, Ekaterina S., et al., "Structures of ligand-occupied β-Klotho complexes reveal a molecular mechanism underlying endocrine FGF specificity and activity", Proceedings of the National Academy of Sciences116 (16), Apr. 2019, 7819-7824.
Lee, Sangwon, et al., "Structures of β-klotho reveal a 'zip code'-like mechanism for endocrine FGF signaling", Nature, 553 (7689), Jan. 25, 2018, 501-505.
Shalhoub, V., et al., "Fibroblast growth factor 23 (FGF23) and alpha-klotho stimulate osteoblastic MC3T3.E1 cell proliferation and inhibit mineralization", Calcif Tissue Int. 89, Jun. 3, 2011, 140-150.
Yamazaki, Yuji, et al., "Anti-FGF23 Neutralizing Antibodies Show the Physiological Role and Structural Features of FGF23", Journal of Bone and Mineral Research 23(9), Apr. 21, 2008, 1509:1518.

* cited by examiner

*Primary Examiner* — Christine J Saoud
(74) *Attorney, Agent, or Firm* — Domingos J. Silva; Kathryn Doyle; Saul Ewing Arnstein & Lehr LLP

(57) ABSTRACT

The present invention relates, in one aspect, to certain mutant FGF21 polypeptide constructs. In certain non-limiting embodiments, the construct binds to β-Klotho more tightly than wild-type FGF21. In certain non-limiting embodiments, the construct has a mutation in at least one residue of SEQ ID NO:3 selected from the group consisting of V188, R203, and L194. In certain non-limiting embodiments, the construct further comprises a stability enhancing domain.

5 Claims, 20 Drawing Sheets

Specification includes a Sequence Listing.

FIG. 2A
FIG. 2B
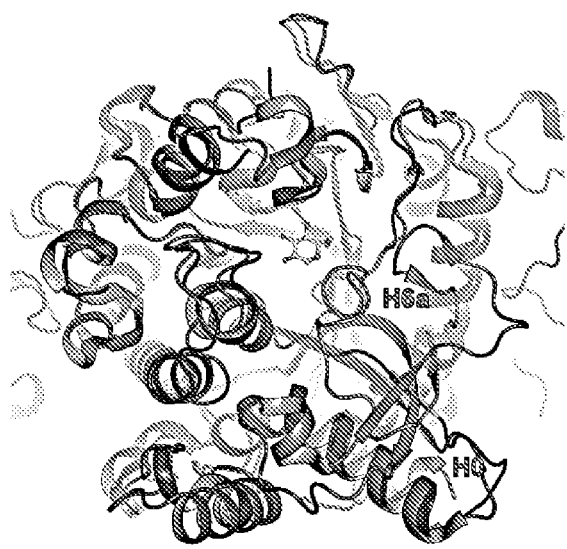
FIG. 2C
FIG. 2D
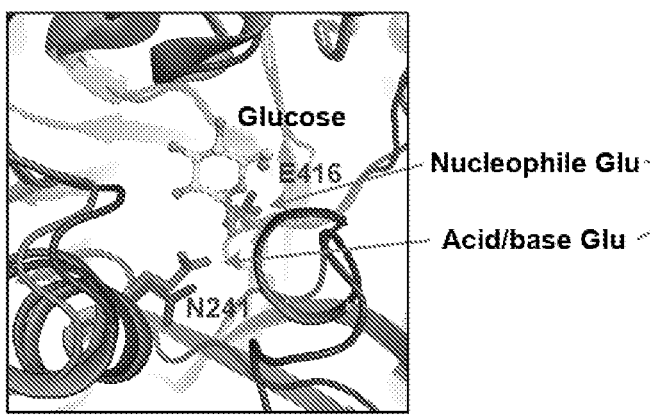
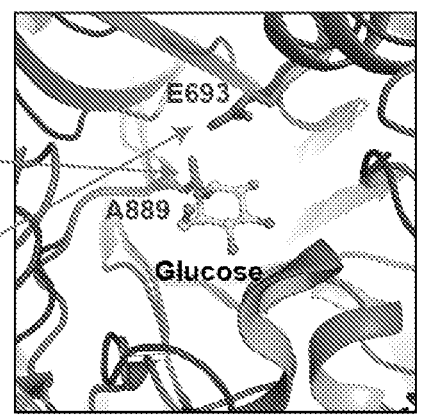
FIG. 2E
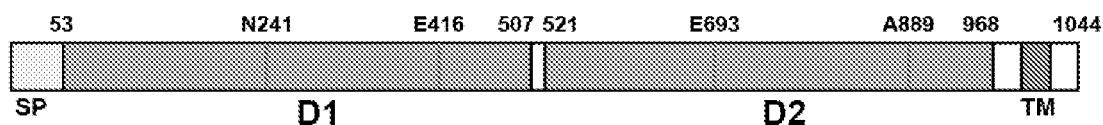

(left panel)

(right panel)

SEQUENCE LISTING

<160> NUMBER OF SEQ ID NOS: 3

<210> SEQ ID NO 1
<211> LENGTH: 1044
<212> TYPE: PRT
<213> ORGANISM: Artificial Sequence
<220> FEATURE:
<223> OTHER INFORMATION: beta-Klotho

<400> SEQUENCE: 1

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
```

```
                    355                 360                 365
Phe Phe Ala Phe Ser Phe Gly Pro Asn Asn Phe Lys Pro Leu Asn Thr
370                 375                 380
Met Ala Lys Met Gly Gln Asn Val Ser Leu Asn Leu Arg Glu Ala Leu
385                 390                 395                 400
Asn Trp Ile Lys Leu Glu Tyr Asn Asn Pro Arg Ile Leu Ile Ala Glu
                    405                 410                 415
Asn Gly Trp Phe Thr Asp Ser Arg Val Lys Thr Glu Asp Thr Thr Ala
                420                 425                 430
Ile Tyr Met Met Lys Asn Phe Leu Ser Gln Val Leu Gln Ala Ile Arg
            435                 440                 445
Leu Asp Glu Ile Arg Val Phe Gly Tyr Thr Ala Trp Ser Leu Leu Asp
        450                 455                 460
Gly Phe Glu Trp Gln Asp Ala Tyr Thr Ile Arg Arg Gly Leu Phe Tyr
465                 470                 475                 480
Val Asp Phe Asn Ser Lys Gln Lys Glu Arg Lys Pro Lys Ser Ser Ala
                485                 490                 495
His Tyr Tyr Lys Gln Ile Ile Arg Glu Asn Gly Phe Ser Leu Lys Glu
                500                 505                 510
Ser Thr Pro Asp Val Gln Gly Gln Phe Pro Cys Asp Phe Ser Trp Gly
            515                 520                 525
Val Thr Glu Ser Val Leu Lys Pro Glu Ser Val Ala Ser Ser Pro Gln
        530                 535                 540
Phe Ser Asp Pro His Leu Tyr Val Trp Asn Ala Thr Gly Asn Arg Leu
545                 550                 555                 560
Leu His Arg Val Glu Gly Val Arg Leu Lys Thr Arg Pro Ala Gln Cys
                565                 570                 575
Thr Asp Phe Val Asn Ile Lys Lys Gln Leu Glu Met Leu Ala Arg Met
                580                 585                 590
Lys Val Thr His Tyr Arg Phe Ala Leu Asp Trp Ala Ser Val Leu Pro
            595                 600                 605
Thr Gly Asn Leu Ser Ala Val Asn Arg Gln Ala Leu Arg Tyr Tyr Arg
        610                 615                 620
Cys Val Val Ser Glu Gly Leu Lys Leu Gly Ile Ser Ala Met Val Thr
625                 630                 635                 640
Leu Tyr Tyr Pro Thr His Ala His Leu Gly Leu Pro Glu Pro Leu Leu
                645                 650                 655
His Ala Asp Gly Trp Leu Asn Pro Ser Thr Ala Glu Ala Phe Gln Ala
                660                 665                 670
Tyr Ala Gly Leu Cys Phe Gln Glu Leu Gly Asp Leu Val Lys Leu Trp
            675                 680                 685
Ile Thr Ile Asn Glu Pro Asn Arg Leu Ser Asp Ile Tyr Asn Arg Ser
        690                 695                 700
Gly Asn Asp Thr Tyr Gly Ala Ala His Asn Leu Leu Val Ala His Ala
705                 710                 715                 720
Leu Ala Trp Arg Leu Tyr Asp Arg Gln Phe Arg Pro Ser Gln Arg Gly
                725                 730                 735
Ala Val Ser Leu Ser Leu His Ala Asp Trp Ala Glu Pro Ala Asn Pro
                740                 745                 750
Tyr Ala Asp Ser His Trp Arg Ala Ala Glu Arg Phe Leu Gln Phe Glu
            755                 760                 765
Ile Ala Trp Phe Ala Glu Pro Leu Phe Lys Thr Gly Asp Tyr Pro Ala
        770                 775                 780
```

```
Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
            805                 810                 815

Thr Val Asp Phe Cys Ala Leu Asn His Phe Thr Thr Arg Phe Val Met
        820                 825                 830

His Glu Gln Leu Ala Gly Ser Arg Tyr Asp Ser Asp Arg Asp Ile Gln
    835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
    1025                1030                1035

Gly Lys Arg Val Val Ser
    1040

<210> SEQ ID NO 2
<211> LENGTH: 216
<212> TYPE: PRT
<213> ORGANISM: Artificial Sequence
<220> FEATURE:
<223> OTHER INFORMATION: FGF19

<400> SEQUENCE: 2

Met Arg Ser Gly Cys Val Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95
```

```
Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 3
<211> LENGTH: 209
<212> TYPE: PRT
<213> ORGANISM: Artificial Sequence
<220> FEATURE:
<223> OTHER INFORMATION: FGF21

<400> SEQUENCE: 3

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

MUTANT FGF21 POLYPEPTIDE COMPOSITIONS

CROSS-REFERENCE TO RELATED APPLICATIONS

This application is a 35 U.S.C. § 371 national phase application of, and claims priority to, International Application No. PCT/US2018/040932, filed Jul. 5, 2018, which claims priority under 35 U.S.C. § 119(e) to U.S. Provisional Application No. 62/529,215, filed Jul. 6, 2017, the disclosures of all of which are incorporated herein by reference in their entireties.

BACKGROUND OF THE INVENTION

Cellular signaling initiated by fibroblast growth factors (FGFs) controls important physiological processes during normal embryonic development and homeostasis in adult animals. Accordingly, a variety of diseases are caused by genetic disruption or aberrant regulation of FGF-dependent cell signaling pathways. The 22 members of the FGF family stimulate their cellular responses by binding to the extracellular domains of four members of the fibroblast growth factor receptors (FGFRs), which are a family of receptor tyrosine kinases (RTKs).

Canonical FGFs activate FGFRs through paracrine or autocrine mechanisms, in a process that requires the action of an FGF ligand together with heparan sulfate proteoglycans (HSPG) that function as critical co-receptors for FGFs. This requirement for HSPGs distinguishes FGFRs from most other RTKs, which are typically activated directly by specific growth factor binding to the extracellular domains of a cognate receptor. Receptor dimerization is crucial for FGFR activation as with other RTKs. In contrast with other growth factors such as EGF and PDGF, however, canonical FGFs can stimulate FGFR dimerization only when bound to HSPGs. FGFR dimerization leads to kinase activation and trans-phosphorylation of specific tyrosine residues in the receptor cytoplasmic domain. This, in turn, triggers stimulation of multiple signaling pathways, either through direct association of signaling molecules with activated FGFR or through indirect interactions mediated by closely associated docking proteins such as FRS2 and Gab1, specialized in recruiting unique complements of signaling proteins.

FGF19, FGF21, and FGF23 stand out from the canonical FGFs by exhibiting hallmarks of circulating hormones, and are thus termed endocrine FGFs. FGF19 and FGF21 both function as hormones that bind specifically to receptors located in liver, fat tissue, and the hypothalamus and regulate metabolic functions such as bile acid synthesis and lipogenesis, and also stimulate insulin sensitivity, energy expenditure and weight loss. The target organs of FGF23 are kidney and parathyroid—FGF23 binding stimulates urinary phosphate excretion and decreases parathyroid hormone levels, respectively. Unlike canonical FGFs that require HSPG to activate FGFRs, endocrine FGFs do not have this requirement, but instead are specifically dependent on Klotho co-receptors for FGFR activation.

There are two Klothos, encoded by different genes. α-Klotho is required for FGF23-dependent signaling, and β-Klotho is essential for FGF19- or FGF21-dependent signaling in specific tissues and organs. Although different FGFRs are expressed throughout the body, expression of Klotho proteins is limited to specific tissues—α-Klotho expression is confined to the kidney and parathyroid, whereas β-Klotho expression is limited to adipose tissue, liver, pancreas and hypothalamus. Both Klotho proteins are membrane receptors composed of an N-terminal extracellular region and a single transmembrane spanning region followed by a short cytoplasmic region. Each Klotho extracellular region contains tandem domains that share sequence similarity with the glycoside hydrolase family of enzymes. Amino acid sequence alignments indicate that one of the two catalytic amino acid residues of each of Klotho's glycoside hydrolase-like domains (GH domain) were substituted at some point in its evolution, indicating that Klotho's GH domains are deficient in enzymatic activity and can be defined as pseudo-enzymes. However, several reports have suggested that α-Klotho has some detectable enzymatic activity.

There is a need in the art to identify compositions and methods that can be used to modulate (e.g. inhibit or stimulate) the activity of FGF receptors and the signaling pathways activated by endocrine FGFs. In certain embodiments, these compositions and methods are useful in treating, ameliorating and/or preventing diseases (such as, but not limited to, metabolic diseases and/or cancer) associated with endocrine FGFs. The present invention fulfills these needs.

BRIEF SUMMARY OF THE INVENTION

The invention provides a non-natural soluble construct that prevents or minimizes the binding of at least one selected from the group consisting of a FGF receptor (FGFR), FGF19, and FGF21, to β-Klotho.

In certain embodiments, the β-Klotho is on the surface of a mammal's cell.

In certain embodiments, the construct is at least selected from the group consisting of an antibody, nanobody, recombinant protein, and small molecule. In other embodiments, the construct is at least one selected from the group consisting of an antibody and a recombinant peptide. In yet other embodiments, the antibody is at least one selected from the group consisting of a polyclonal antibody, monoclonal antibody, humanized antibody, synthetic antibody, heavy chain antibody, human antibody, biologically active fragment of an antibody, and any combinations thereof.

In certain embodiments, the construct recognizes and binds to at least one amino acid residue of FGF19 or FGF21 that binds to β-Klotho, thus preventing FGF19 or FGF21 binding to β-Klotho.

In certain embodiments, the construct recognizes and binds to at least one amino acid within the amino acid residues 169-209 in FGF21 (SEQ ID NO:3).

In certain embodiments, the construct recognizes and binds to at least one amino acid within the amino acid residues 186-209 in SEQ ID NO:3.

In certain embodiments, the construct recognizes and binds to at least one amino acid within the amino acid residues 170-216 in $FGF19_{CT}$ (SEQ ID NO:2).

In certain embodiments, the construct recognizes and/or binds to at least one amino acid residue of β-Klotho that binds to FGF19 or FGF21, thus preventing β-Klotho binding to FGF19 or FGF21.

In certain embodiments, the construct recognizes and/or binds to one or more amino acids within the amino acid residues 379-942 in β-Klotho (SEQ ID NO:1).

In certain embodiments, the construct recognizes and/or binds to one or more amino acids within amino acids 379-380, 392-394, 419-422, 431, 434-435, 438, 532, 643-

647, 692-694, 696-697, 743, 745, 764, 768, 824, 826, 829, 832, 845, 847-851, 853, 862, 889, 931-932, 939-940, and 942 in SEQ ID NO:1.

In certain embodiments, the construct recognizes and binds to at least one amino acid residue of β-Klotho that binds to a FGFR, thus preventing β-Klotho binding to the FGFR.

In certain embodiments, the construct recognizes and/or binds to one or more amino acids within the extracellular region of human β-Klotho (amino acid residues 53-983 of SEQ ID NO:1), or a fragment thereof.

In certain embodiments, the construct recognizes and/or binds to one or more amino acids within the fragment of the extracellular region of human β-Klotho comprising amino acid residues 533-575 of SEQ ID NO:1.

In certain embodiments, the construct comprises at least one selected from the group consisting of a FGF19 polypeptide and FGF21 polypeptide that is capable of binding to and sequestering β-Klotho on the surface of a mammal's cell. In other embodiments, the construct comprises amino acid residues 169-209 of SEQ ID NO:3 (FGF21$_{CT}$). In yet other embodiments, the construct comprises amino acid residues 170-216 of SEQ ID NO:2 (FGF19$_{CT}$).

In certain embodiments, the construct comprises a β-Klotho polypeptide that is capable of binding to and sequestering at least one selected from the group consisting of FGF19 and FGF21. In other embodiments, the β-Klotho polypeptide comprises the extracellular region of human β-Klotho (amino acids 53-983 of SEQ ID NO:1), or a fragment thereof. In yet other embodiments, the Klotho polypeptide comprises the fragment of the extracellular region of human β-Klotho comprising amino acids 379-942 of SEQ ID NO:1.

In certain embodiments, the construct comprises a β-Klotho polypeptide that is capable of binding to a FGFR. In other embodiments, the construct comprises the extracellular region of human β-Klotho (amino acid residues 53-983 of SEQ ID NO:1), or a fragment thereof. In yet other embodiments, the construct comprises amino acid residues 533-575 of SEQ ID NO:1.

The invention further provides a soluble construct comprising at least one selected from the group consisting of a FGF19 polypeptide and FGF21 polypeptide that binds to β-Klotho more tightly than at least one selected from the group consisting of wild-type FGF19 and wild-type FGF21.

In certain embodiments, the at least one selected from the group consisting of FGF19 polypeptide and FGF21 polypeptide has at least one mutation in its C-terminal domain. In other embodiments, the FGF21 polypeptide has a mutation in at least one residue selected from the group consisting of V188, R203 and L194. In yet other embodiments, the FGF21 polypeptide has at least one mutation selected from the group consisting of R203W and L194F. In yet other embodiments, The invention further provides a construct that simultaneously binds to an exposed epitope on FGF21$_{CT}$ and an exposed epitope on β-Klotho in a FGF21$_{CT}$-β-Klotho complex, thus stabilizing the FGF21$_{CT}$-β-Klotho complex.

In certain embodiments, the construct is at least one selected from the group consisting of an antibody, nanobody, recombinant protein, and small molecule. In other embodiments, the construct is at least one selected from the group consisting of an antibody and a recombinant peptide. In yet other embodiments, the antibody is selected from the group consisting of a polyclonal antibody, monoclonal antibody, humanized antibody, synthetic antibody, heavy chain antibody, human antibody, biologically active fragment of an antibody, and any combinations thereof.

A construct comprising a β-Klotho binder fused to at least one selected from the group consisting of a FGF19 polypeptide and FGF21 polypeptide, wherein the construct has at least one selected from the group consisting of FGF19 stimulatory activities and FGF 21 stimulatory activities.

In certain embodiments, the construct of the invention is fused to a stability enhancing domain. In other embodiments, the stability enhancing domain comprises at least one selected from the group consisting of albumin, thioredoxin, glutathione S-transferase, and a Fc region of an antibody. In yet other embodiments, the polypeptide and the stability enhancing domain are linked through a polypeptide comprising about 1-18 amino acids.

The invention further provides a method of treating and/or preventing endocrine FGF-related diseases or disorders in a mammal in need thereof.

In certain embodiments, the method comprises administering to the mammal a therapeutically effective amount of a construct that modulates interaction of at least one selected from the group consisting of FGF19 and FGF21 with β-Klotho on the surface of a cell of the mammal. In other embodiments, the construct prevents or minimizes binding of at least one selected from the group consisting of FGF19 and FGF21 to β-Klotho on the surface of the mammal's cell. In other embodiments, the disease or disorder comprises at least one selected from the group consisting of liver cancer and colon cancer. In yet other embodiments, the construct binds more tightly than at least one selected from the group consisting of wild-type FGF19 and wild-type FGF21 to β-Klotho on the surface of the mammal's cell. In yet other embodiments, the disease or disorder comprises at least one selected from the group consisting of obesity, diabetes, pancreatitis, nonalcoholic fatty liver disease (NAFLD), and nonalcoholic steatohepatitis (NASH).

In certain embodiments, the mammal is human. In other embodiments, the construct is administered by at least one route selected from the group consisting of inhalational, oral, rectal, vaginal, parenteral, intracranial, topical, transdermal, pulmonary, intranasal, buccal, ophthalmic, intrathecal, and intravenous. In yet other embodiments, the mammal is further administered at least one additional drug that treats or prevents the disease and/or disorder. In yet other embodiments, the construct and the at least one additional drug are co-administered. In yet other embodiments, the construct and the at least one additional drug are co-formulated.

BRIEF DESCRIPTION OF THE DRAWINGS

For the purpose of illustrating the invention, certain embodiments of the invention are depicted in the drawings. However, the invention is not limited to the precise arrangements and instrumentalities of the embodiments depicted in the drawings.

FIGS. 2A-2E illustrate an exemplary structural comparison of sKLB with human cytosolic β-glucosidase. The structure of human cytosolic β-glucosidase (red, PDB: 2ZOX) is superimposed with D1 (FIG. 2A) and D2 (FIG. 2B) of sKLB (blue) with overall α-carbon root-mean-square deviations (RMSDs) of 1.08 Å and 1.39 Å, respectively.

Regions in sKLB that are different from β-glucosidase are colored in green, and regions in β-glucosidase that are different from sKLB are colored in grey. A glucose molecule bound to β-glucosidase is shown as ball-and-stick representation in yellow. Superimposition of D1 (FIG. 2C) and D2 (FIG. 2D) to reveal locations of "catalytic" glutamates. One of the two catalytic glutamates from each of sKLB domains is replaced by an asparagine (for D1) or an alanine (for D2). FIG. 2E: Diagram of KLB highlighting the locations of the residues corresponding to the catalytic glutamates in D1 and D2 of sKLB.

FIG. 3C: Residues interacting between sKLB (green) and FGF21$_{CT}$ (salmon) in site 1 and site 2 areas are indicated. FIGS. 3D-3E: Diagram of amino acid-specific interactions between sKLB and FGF21$_{CT}$ within site 1 (FIG. 3D) and site 2 (FIG. 3E).

FIG. 4A: Surface representation of sKLB (green) highlighting two binding sites, site 1 and site 2 of FGF21$_{CT}$ (salmon, ball-and-stick). FIG. 4B: Site 1 forms a series of internal hydrogen bonds (black dashed lines) through three consecutive turns (orange, yellow, and light blue), creating a structural element that binds to D1 of sKLB. FIG. 4C: Site 2 interacts with pseudo-substrate binding region of D2 of sKLB.

FIG. 5C: Superimposition of the structures of cellopentaose-bound rice β-glucosidase and FGF21$_{CT}$-bound sKLB. FIG. 5D: E693 (the single "catalytic" glutamic acids) of β-Klotho makes contacts with S—P—S motif of FGF21 through interaction with hydroxyl moieties of serines mimicking sugar hydroxyls in their interaction with glutamates in the catalytic site of β-glucosidase. FIG. 5E: Schematic diagram comparing the substrate-binding pocket including the two glutamates required for glycoside hydrolase activity and the ligand-binding pocket of β-Klotho depicting interactions between E693 with the S—P—S motif.

FIG. 6E: Location of mutated amino acid residues (yellow) in sKLB (green) occupied by FGF21 (salmon) that were analyzed in panels F and G. FIGS. 6F-6G: stably transfected L6 cells co-expressing FGFR1c together with WT or β-Klotho mutants were stimulated with either FGF1 or FGF21 and analyzed for FGFR1c activation by monitoring tyrosine phosphorylation of FGFR1c. Lysates of ligand stimulated or unstimulated cells were subjected to immunoprecipitation with anti FGFR1 antibodies followed by immunoblotting with either anti-pTyr or anti-FGFR1 antibodies.

DETAILED DESCRIPTION OF THE INVENTION

Figure 1A:
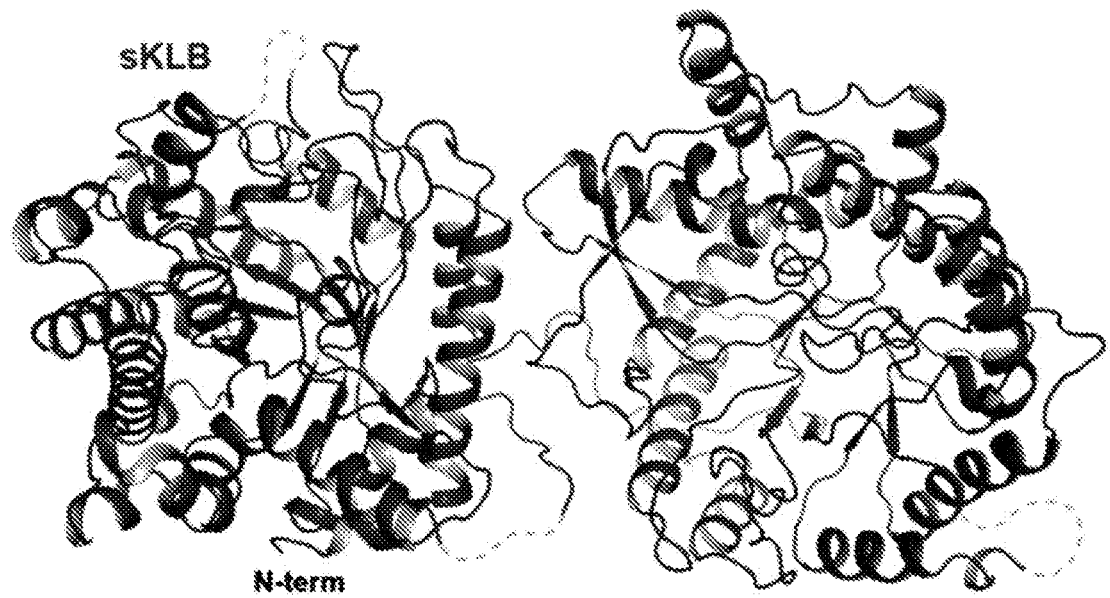
FIGS. 1A-1B illustrate an exemplary crystal structure of extracellular domain of β-Klotho (sKLB), shown as ribbon representation (FIG. 1A) and surface representation (FIG. 1B). Regions that do not show significant electron density are drawn with grey dashed lines.
Figure 1B:
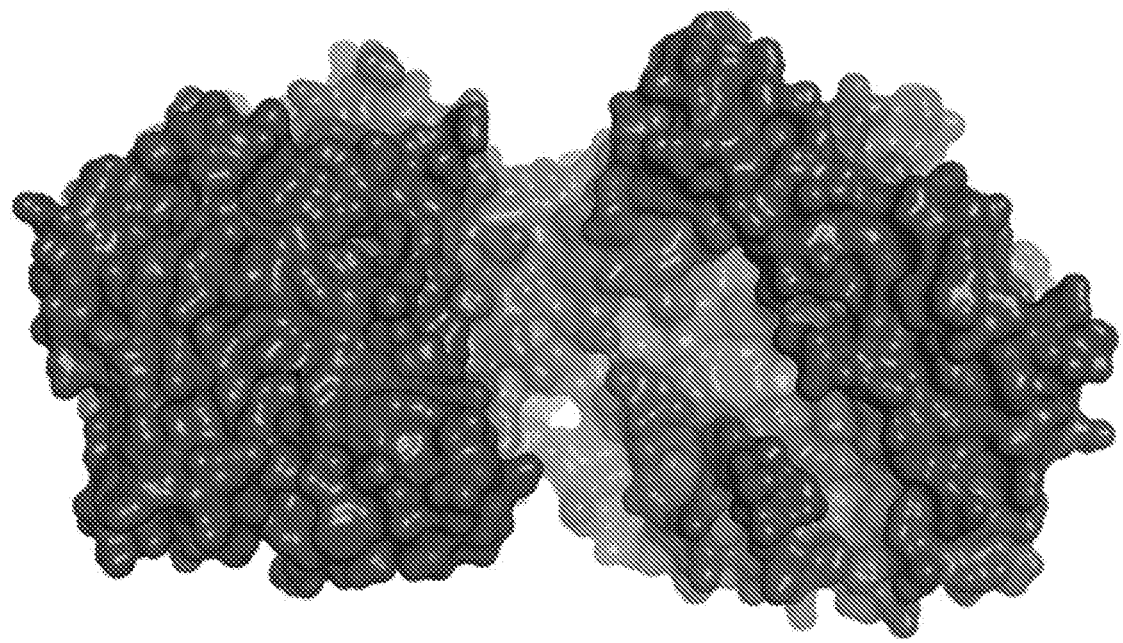

The present invention relates in one aspect to the discovery that β-Klotho is the primary cell-surface receptor for FGF21, with FGFR1c functioning as a catalytic subunit that ultimately mediates intracellular signaling. In one aspect, the invention provides compositions and methods that are useful in treating or preventing endocrine FGF-related diseases or disorders.

FGF19 and FGF21 are circulating hormones that regulate metabolic processes in a variety of tissues. They signal through FGFRs in a manner that requires Klothos, which are cell surface proteins with tandem glycoside hydrolase (GH) domains. The present invention provides crystal structures of the extracellular domain of β-Klotho (sKLB) both alone and complexed with the Klotho-binding region of FGF21. The structural analyses, together with biochemical and cellular experiments, reveal details of the molecular interactions that determine the specificity of FGF21 and other endocrine FGFs towards β-Klotho, and also demonstrate how FGFR is activated in a Klotho-dependent manner. The FGF binding mode seen in the crystal structures further reveals how the serine-rich C-terminal tail of FGF21 presents hydroxyl groups to mimic a carbohydrate bound in the vestigial active site of a Klotho glycoside hydrolase domain. This unexpected mode of FGF21 recognition by Klotho, together with mechanistic insights into how Klotho promotes FGFR activation, provide a rational roadmap for the development of novel therapeutics for metabolic and other diseases associated with endocrine FGFs and their signaling pathways.

Definitions

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, crystallography, and chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, the term "β-Klotho" refers to the protein of amino sequence of SEQ ID NO:1:

```
         10         20         30         40
MKPGCAAGSP GNEWIFFSTD EITTRYRNTM SNGGLQRSVI 50         60         70         80
LSALILLRAV TGFSGDGRAI WSKNPNFTPV NESQLFLYDT 90        100        110        120
FPKNFFWGIG TGALQVEGSW KKDGKGPSIW DHFIHTHLKN 130        140        150        160
VSSTNGSSDS YIFLEKDLSA LDFIGVSFYQ FSISWPRLFP 170        180        190        200
DGIVTVANAK GLQYYSTLLD ALVLRNIEPI VTLYHWDLPL 210        220        230        240
ALQEKYGGWK NDTIIDIFND YATYCFQMFG DRVKYWITIH 250        260        270        280
NPYLVAWHGY GTGMHAPGEK GNLAAVYTVG HNLIKAHSKV 290        300        310        320
WHNYNTHFRP HQKGWLSITL GSHWIEPNRS ENTMDIFKCQ 330        340        350        360
QSMVSVLGWF ANPIHGDGDY PEGMRKKLFS VLPIFSEAEK 370        380        390        400
HEMRGTADFF AFSFGPNNFK PLNTMAKMGQ NVSLNLREAL 410        420        430        440
NWIKLEYNNP RILIAENGWF TDSRVKTEDT TAIYMMKNFL 450        460        470        480
SQVLQAIRLD EIRVFGYTAW SLLDGFEWQD AYTIRRGLFY 490        500        510        520
VDFNSKQKER KPKSSAHYYK QIIRENGFSL KESTPDVQGQ 530        540        550        560
FPCDFSWGVT ESVLKPESVA SSPQFSDPHL YVWNATGNRL 570        580        590        600
LHRVEGVRLK TRPAQCTDFV NIKKQLEMLA RMKVTHYRFA 610        620        630        640
LDWASVLPTG NLSAVNRQAL RYYRCVVSEG LKLGISAMVT
```

-continued
```
        650        660        670        680
LYYPTHAHLG LPEPLLHADG WLNPSTAEAF QAYAGLCFQE 690        700        710        720
LGDLVKLWIT INEPNRLSDI YNRSGNDTYG AAHNLLVAHA 730        740        750        760
LAWRLYDRQF RPSQRGAVSL SLHADWAEPA NPYADSHWRA 770        780        790        800
AERFLQFEIA WFAEPLFKTG DYPAAMREYI ASKHRRGLSS 810        820        830        840
SALPRLTEAE RRLLKGTVDF CALNHFTTRF VMHEQLAGSR 850        860        870        880
YDSDRDIQFL QDITRLSSPT RLAVIPWGVR KLLRWVRRNY 890        900        910        920
GDMDIYITAS GIDDQALEDD RLRKYYLGKY LQEVLKAYLI 930        940        950        960
DKVRIKGYYA FKLAEEKSKP RFGFFTSDFK AKSSIQFYNK 970        980        990       1000
VISSRGFPFE NSSSRCSQTQ ENTECTVCLF LVQKKPLIFL 1010       1020       1030       1040
GCCFFSTLVL LLSIAIFQRQ KRRKFWKAKN LQHIPLKKGK RVVS
```

As used herein, the extracellular domain of β-Klotho (sKLB) corresponds to the amino acid residues 53-983 of SEQ ID NO:1.

The term "antibody," as used herein, refers to an immunoglobulin molecule that specifically binds with an antigen. Antibodies can be intact immunoglobulins derived from natural sources or from recombinant sources, and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, single-domain antibodies such as sdAb (either VL or VH), such as camelid antibodies (Riechmann, 1999, J. Immunol. Meth. 231:25-38), camelid VHH domains, composed of either a VL or a VH domain that exhibit sufficient affinity for the target, and multispecific antibodies formed from antibody fragments such as a bivalent fragment comprising two Fab fragments linked by a disulfide brudge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger & Hudson, 2005, Nature Biotech. 23:1126-1136). Antigen binding fragments can also be grafted into scaffolds based on polypeptides such as a fibronectin type III (Fn3)(U.S. Pat. No. 6,703,199, which describes fibronectin polypeptide minibodies). The antibody fragment also includes a human antibody or a humanized antibody or a portion of a human antibody or a humanized antibody.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene. A "coding region" of an mRNA molecule also consists of the nucleotide residues of the mRNA molecule that are matched with an anti-codon region of a transfer RNA molecule during translation of the mRNA molecule or that encode a stop codon. The coding region may thus include nucleotide residues corresponding to amino acid residues that are not present in the mature protein encoded by the mRNA molecule (e.g., amino acid residues in a protein export signal sequence).

A "constitutive" promoter is a nucleotide sequence that, when operably linked with a polynucleotide that encodes or specifies a gene product, causes the gene product to be produced in a cell under most or all physiological conditions of the cell.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound which is sufficient to provide a beneficial effect to the subject to which the compound is administered.

As used herein, "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, may be referred to as encoding the protein or other product of that gene or cDNA.

As used herein "endogenous" refers to any material from or produced inside an organism, cell, tissue or system. As used herein, the term "exogenous" refers to any material introduced from or produced outside an organism, cell, tissue or system.

The term "epitope" as used herein is defined as a small chemical molecule on an antigen that may elicit an immune response, inducing B and/or T cell responses. An antigen may have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cisacting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "FGF19" refers to a polypeptide of SEQ ID NO:2:

```
          10         20         30         40
MRSGCVVVHV WILAGLWLAV AGRPLAFSDA GPHVHYGWGD 50         60         70         80
PIRLRHLYTS GPHGLSSCFL RIRADGVVDC ARGQSAHSLL 90        100        110        120
EIKAVALRTV AIKGVHSVRY LCMGADGKMQ GLLQYSEEDC 130        140        150        160
AFEEEIRPDG YNVYRSEKHR LPVSLSSAKQ RQLYKNRGFL 170        180        190        200
PLSHFLPMLP MVPEEPEDLR GHLESDMFSS PLETDSMDPF

210
GLVTGLEAVR SPSFEK
```

As used herein, "FGF19$_{CT}$" refers to a polypeptide corresponding to the amino acid residues 170-216 of SEQ ID NO:2.

As used herein, the term "FGF21" refers to a polypeptide of SEQ ID NO:3:

```
          10         20         30         40
MDSDETGFEH SGLWVSVLAG LLLGACQAHP IPDSSPLLQF 50         60         70         80
GGQVRQRYLY TDDAQQTEAH LEIREDGTVG GAADQSPESL 90        100        110        120
LQLKALKPGV IQILGVKTSR FLCQRPDGAL YGSLHFDPEA 130        140        150        160
CSFRELLLED GYNVYQSEAH GLPLHLPGNK SPHRDPAPRG 170        180        190        200
PARFLPLPGL PPALPEPPGI LAPQPPDVGS SDPLSMVGPS

QGRSPSYAS
```

As used herein, "FGF21$_{CT}$" refers to a polypeptide corresponding to the amino acid residues 169-209 of SEQ ID NO:3, which in certain embodiments contains two mutations, P199G and A208E (see US 20120087920, which is incorporated herein in its entirety by reference)

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of V$_H$ (variable heavy chain immunoglobulin) genes from an animal.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 5'-ATTGCC-3' and 5'-TATGGC-3' share 50% homology.

As used herein, the term "immunoglobulin" or "Ig" is defined as a class of proteins that function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitor-urinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

An "inducible" promoter is a nucleotide sequence that, when operably linked with a polynucleotide that encodes or specifies a gene product, causes the gene product to be produced in a cell substantially only when an inducer that corresponds to the promoter is present in the cell.

The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the co-existing materials of its natural state is "isolated." An isolated nucleic acid or protein may exist in substantially purified form, or may exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences that are normally adjacent to the fragment, i.e., the sequences adjacent to the fragment in a genome in which it naturally occurs. The term also applies to nucleic acids that have been substantially purified from other components which naturally accompany the nucleic acid, i.e., RNA or DNA or proteins, which naturally accompany it in the cell. The term therefore includes, for example, a recombinant DNA that is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA that is part of a hybrid gene encoding additional polypeptide sequence.

As used herein, the term "modulate" is meant to refer to any change in biological state, i.e. increasing, decreasing, and the like. For example, the term "modulate" may be construed to refer to the ability to regulate positively or negatively the expression, stability or activity of a target protein, including but not limited to transcription of a target protein mRNA, stability of a target protein mRNA, translation of a target protein mRNA, target protein stability, target protein post-translational modifications, target protein activity, or any combination thereof. Further, the term modulate may be used to refer to an increase, decrease, masking, altering, overriding or restoring of activity, including but not limited to, target protein activity.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of a composition includes, e.g., subcutaneous (s.c.), intravenous (i.v.), intramuscular (i.m.), or intrasternal injection, or infusion techniques.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary, intracranial and topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

"Pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus. As used herein, a "peptidomimetic" is a compound containing non-peptidic structural elements that is capable of mimicking the biological action of a parent peptide. A peptidomimetic may or may not comprise peptide bonds.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes may be labeled with, e.g., chromogenic, radioactive, or fluorescent moieties and used as detectable moieties.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements that are required for expression of the gene product. The promoter/regulatory sequence may for example be one that expresses the gene product in a tissue specific manner.

The term "recombinant DNA" as used herein is defined as DNA produced by joining pieces of DNA from different sources. The term "recombinant polypeptide" as used herein is defined as a polypeptide produced by using recombinant DNA methods.

The term "RNA" as used herein is defined as ribonucleic acid.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

As used herein, a "subject" refers to a human or non-human mammal. Non-human mammals include, for example, livestock and pets, such as ovine, bovine, porcine, canine, feline and murine mammals. In certain embodiments, the subject is human.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "tissue-specific" promoter is a nucleotide sequence that, when operably linked with a polynucleotide encodes or specified by a gene, causes the gene product to be produced in a cell substantially only if the cell is a cell of the tissue type corresponding to the promoter.

The term "transfected" or "transformed" or "transduced" as used herein refers to a process by which exogenous nucleic acid is transferred or introduced into the host cell. A "transfected" or "transformed" or "transduced" cell is one that has been transfected, transformed or transduced with exogenous nucleic acid. The cell includes the primary subject cell and its progeny.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics. An appropriate therapeutic amount in any individual case may be determined by one of ordinary skill in the art using routine experimentation.

The phrase "under transcriptional control" or "operatively linked" as used herein means that the promoter is in the correct location and orientation in relation to a polynucleotide to control the initiation of transcription by RNA polymerase and expression of the polynucleotide.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide may differ in amino acid sequence by one or more substitutions, additions, or deletions in any combination. A variant of a nucleic acid or peptide may be a naturally occurring such as an allelic variant, or may be a variant that is not known to occur naturally. Non-naturally occurring variants of nucleic acids and peptides may be made by mutagenesis techniques or by direct synthesis.

A "vector" is a composition of matter that comprises an isolated nucleic acid and that may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Abbreviation used herein include: FGF, fibroblast growth factor; FGFR, fibroblast growth factor receptor; GDNF, glial cell-derived neurotrophic factor; GH domain, glycoside hydrolase-like domain; HSPG, heparan sulfate proteoglycans; MES, 2-(N-morpholino) ethanesulfonic acid; RMSD, root-mean-square deviation; RTK, receptor tyrosine kinase; sKLB, extracellular domain of β-Klotho.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Disclosure

In one aspect, the invention provides compositions and methods that are useful in treating endocrine FGF-related diseases or disorders. In certain embodiments, the compositions of the invention prevent or minimize the binding of FGF21 (and/or FGF19 and/or FGFR) to β-Klotho on the surface of a mammal's cell. In other embodiments, the compositions of the invention bind more tightly than wild-type FGF19 and/or FGF21 to β-Klotho on the surface of a mammal's cell.

As discussed herein, the two members of the Klotho family play important roles in mediating signaling by the three endocrine FGFs that function as circulating hormones to regulate an array of metabolic processes, including lowering of blood sugar. Because endocrine FGFs can activate FGFRs only in cells that also express either α-Klotho or β-Klotho, it was proposed that Klotho proteins function as co-receptors for FGFR activation, similar to the role-played by HSPGs as co-receptors for FGFR activation by canonical FGFs. For canonical FGFs, HSPGs play two primary but interdependent roles in FGFR activation. First, binding of HSPGs to both FGF and FGFR to form stable ternary HSPG/FGF/FGFR complexes appears to compensate for the relatively low (micromolar-range) affinities of canonical FGFs for FGFRs. The $K_D$ value for binding of canonical FGFs to their receptors is approximately 1000-fold weaker than binding of EGF or PDGF to their cognate RTKs. Second, HSPGs, through formation of HSPG/FGF/FGFR ternary complexes, stabilize receptor dimerization induced by bivalent FGF binding to two FGFR molecules. FGF21 has an even lower affinity for FGFRs (>10-100 04), although it is clear that all three endocrine FGFs must bind FGFRs in order to promote signaling.

The studies described herein reveal that, rather than simply serving as an alternative co-receptor for FGFR1c activation by endocrine FGFs, β-Klotho in fact functions as the primary high affinity receptor for FGF21. The scheme presented in FIG. 7C depicts a non-limiting model for how FGF21 binding to β-Klotho allows it to activate a β-Klotho/FGFR complex to promote tyrosine kinase activation and cell signaling. In the model, FGFR1c and β-Klotho monomers exist in equilibrium with FGFR/β-Klotho hetero-dimers in the membrane. With a $K_D$ of ~1 μM for binding of the FGFR1c$_{D2D3}$ extracellular region to sKLB (FIG. 6B), a substantial portion of FGFR1c and β-Klotho is associated with one another at levels around 10,000 copies per cell. FGF21 binds with high affinity ($K_D$=43.5 nM, FIG. 6A), either to β-Klotho monomers or to preexisting β-Klotho/FGFR1c hetero-dimers. With FGF21 thus tethered through its C-terminal tail to β-Klotho monomers and/or β-Klotho/FGFR1c heterodimers, all three components are reduced to two dimensions at the membrane and the weak (but demonstrable) affinity of FGF21's FGF-core for FGFR1c is sufficient to drive formation of the activated ternary FGF21/FGFR1c/β-Klotho complex through a reduced dimensionality effect on the bivalent binding of FGF to two FGFR molecules. In this non-limiting model, β-Klotho functions as a primary high affinity receptor for FGF21, whereas FGFR1c functions as a catalytic subunit that mediates receptor dimerization and intracellular signaling. This mechanism is similar to that seen for RET, the RTK activated by glial cell-derived neurotrophic factors (GDNFs). GDNF and its relatives first bind to specific members of the GDNF-receptor (GDNFR) family of surface proteins. The ligand-occupied GDNFR then forms a ternary complex with the extracellular domain of RET. In this non-limiting context, β-Klotho functions like a GDNFR, and FGFR1c takes the role of RET.

The crystal structure of sKLB bound to FGF21$_{CT}$ also provides clear views of how the two glycoside hydrolase (GH) domains of β-Klotho have been "repurposed" in evolution to specifically recognize FGF21. Comparing the structures of substrate-bound β-glucosidases to the second GH domain of FGF21$_{CT}$-bound β-Klotho reveals how the active-site of an enzyme specialized in cutting sugars has evolved to become a specific and high-affinity cell-surface receptor for circulating hormones that regulate critical metabolic processes including lowering of blood sugars. The C-terminus of FGF21 appears to present a structural mimic of an oligosaccharide, centered on a hydroxyl group-rich region that contains a S—P—S sequence, also conserved in FGF19. The similarities between FGF21 and FGF19 indicate that the specificity of the two hormones towards β-Klotho and their modes of action are similar. Differences in the cellular responses to these two endocrine FGFs are likely to be determined by the altered binding preferences of the two ligands for the different FGFRs, i.e., FGFR1c or FGFR4 for FGF21 or FGF19, respectively.

Compounds and/or Compositions (a) The Invention Provides a Construct That Prevents or Minimizes Binding of β-Klotho to FGF19 and/or FGF21 and/or a FGFR on the Surface of a Mammal's Cell In one aspect, the invention provides a construct (such as, but not limited to, an antibody and/or recombinant peptide) that prevents or minimizes the binding of FGF19 and/or FGF21 to β-Klotho on the surface of a mammal's cell.

In certain embodiments, the construct recognizes and/or binds to at least one amino acid residue of FGF19 or FGF21 that binds to β-Klotho, thus preventing FGF19 or FGF21 binding to β-Klotho. In other embodiments, the construct recognizes and/or binds to one or more amino acids within the amino acid residues 169-209 in FGF21 (SEQ ID NO:3). In yet other embodiments, the construct recognizes and/or binds to one or more amino acids within the amino acid residues 186-209 in SEQ ID NO:3 (see Table 1). In yet other embodiments, the construct recognizes and/or binds to one or more amino acids within the amino acid residues 170-216 in FGF19 (SEQ ID NO:2).

In certain embodiments, the construct recognizes at least one amino acid residue of β-Klotho that binds to FGF19 or FGF21, thus preventing β-Klotho binding to FGF19 or FGF21. In other embodiments, the construct recognizes and/or binds to one or more amino acids within the amino acid residues 379-942 in β-Klotho (SEQ ID NO:1). In yet other embodiments, the construct recognizes and/or binds to one or more amino acids selected from the group consisting of amino acids 379-380, 392-394, 419-422, 431, 434-435, 438, 532, 643-647, 692-694, 696-697, 743, 745, 764, 768, 824, 826, 829, 832, 845, 847-851, 853, 862, 889, 931-932, 939-940, and 942 in SEQ ID NO:1 (see Table 1 and FIGS. 3D-3E)).

In another aspect, the invention provides a construct that prevents or minimizes the binding of β-Klotho to a FGFR on the surface of a mammal's cell.

In certain embodiments, the construct recognizes at least one amino acid residue of β-Klotho that binds to a FGFR, thus preventing β-Klotho binding to the FGFR. In other embodiments, the construct recognizes and/or binds to one or more amino acids within the extracellular region of human β-Klotho (amino acid residues 53-983 of SEQ ID NO:1), or a fragment thereof. In yet other embodiments, the construct recognizes and/or binds to one or more amino acids within the fragment of the extracellular region of human β-Klotho comprising the amino acid residues 533-575 of SEQ ID NO:1.

TABLE 1

Contacts between $FGF21_{CT}$ and sKLB found in the crystal structure. Amino acid residues from sKLB that contain at least one atom within 5 Å of amino acid residues from $FGF21_{CT}$ are listed. See FIGS. 3A-3E.

| $FGF21_{CT}$ | sKLB |
|---|---|
| P186 | V392, S393, L394 |
| D187 | |
| V188 | F379, K380, V392, W419, F420 |
| G189 | K380, F420 |
| S190 | W419, F420 |
| S191 | W419, F420, T421, D422, T431, M435 |
| D192 | W419, T431, M435 |
| P193 | L394, W419, M435 |
| L194 | L394, M435, N438, I853 |
| S195 | |
| M196 | T431, Y434, M435, F849, L850, Q851, I853 |
| V197 | T431, M832, Q848, F849, L850 |
| G198 | Q848, F849, L850 |
| G199 | I847, Q848, F849 |
| S200 | R829, F849 |
| Q201 | R696, H743, D745, F764, E768, R829, R845, F849 |
| G202 | R696 |
| R203 | H646, R696 |
| S204 | E693, R696, H743, F826 |
| P205 | H743, F826, L862, F931, F942 |
| S206 | Y643, P644, T645, N692, E693, N824, F826, A889, F931 |
| Y207 | P644, T645, H646, A647, N692, E693, P694, R696, L697 |
| E208 | H646, K939, P940 |
| S209 | S532, Y643, T645, F931, K932, K939 |

By way of a non-limited example, an antibody is described below as an example of preventing or minimizing binding of β-Klotho to FGF19, FGF21 and/or FGFR. As will be understood by one skilled in the art, any antibody that may recognize and specifically bind to FGF19/FGF21/FGFR/β-Klotho is useful in the present invention. The invention should not be construed to be limited to any one type of antibody, either known or heretofore unknown, provided that the antibody can specifically bind to FGF19/FGF21/FGFR/β-Klotho, and prevent or minimize binding of β-Klotho to FGF19, FGF21 and/or FGFR. Methods of making and using such antibodies are well known in the art. For example, the generation of polyclonal antibodies may be accomplished by inoculating the desired animal with the antigen and isolating antibodies which specifically bind the antigen therefrom. Monoclonal antibodies directed against full length or peptide fragments of a protein or peptide may be prepared using any well-known monoclonal antibody preparation procedures, such as those described, for example, in Harlow et al. (1989, Antibodies, A Laboratory Manual, Cold Spring Harbor, N.Y.) and in Tuszynski et al. (1988, Blood 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein. However, the invention should not be construed as being limited solely to methods and compositions including these antibodies, but should be construed to include other antibodies, as that term is defined elsewhere herein.

In some instances, it is desirable to prepare monoclonal antibodies from various mammalian hosts, such as rodents (e.g., mice), primates (e.g., humans), etc. Descriptions of techniques for preparing such monoclonal antibodies are well known and are described, for example, in Harlow et al., ANTIBODIES: A LABORATORY MANUAL, COLD SPRING HARBOR LABORATORY, Cold Spring Harbor, N.Y. (1988); Harlow et al., USING ANTIBODIES: A LABORATORYMANUAL, (Cold Spring Harbor Press, New York, 1998); Breitling et al., RECOMBINANT ANTIBODIES (Wiley-Spektrum, 1999); and Kohler et al., 1997 Nature 256: 495-497; U.S. Pat. Nos. 5,693,762; 5,693,761; 5,585,089; and 6,180,370.

Nucleic acid encoding an antibody obtained using the procedures described herein may be cloned and sequenced using technology that is available in the art, and is described, for example, in Wright et al. (Critical Rev. Immunol. 1992, 12:125-168) and the references cited therein. Further, the antibody of the invention may be "humanized" using the technology described in Wright et al. (supra) and in the references cited therein, and in Gu et al. (Thrombosis and Hematocyst 1997, 77:755-759).

Alternatively, antibodies may be generated using phage display technology. To generate a phage antibody library, a cDNA library is first obtained from mRNA that is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage that encode the desired antibody may be engineered such that the protein is displayed on the surface thereof in such a manner that it is available for binding to its corresponding binding protein, e.g., the antigen against which the antibody is directed. Thus, when bacteriophage that express a specific antibody are incubated in the presence of a cell that expresses the corresponding antigen, the bacteriophage will bind to the cell. Bacteriophage that do not express the antibody will not bind to the cell. Such panning techniques are well known in the art and are described for example, in Wright et al. (Critical Rev. Immunol. 1992, 12:125-168).

Processes such as those described herein have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage that display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage that encode the Fab portion of an antibody molecule. However, the invention should not be construed to be limited solely to the generation of phage encoding Fab antibodies. Rather, phage that encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J Mol Biol 222:581-597). Palming of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J Mol Biol 248:97-105).

The invention encompasses polyclonal, monoclonal, synthetic antibodies, and the like. One skilled in the art would understand, based upon the disclosure provided herein, that the crucial feature of the antibody of the invention is that the antibody specifically bind with FGF19/FGF21 and/or β-Klotho.

In yet another aspect, the invention provides a soluble construct that is capable of sequestering β-Klotho, FGF19 and/or FGF21 on the surface of a mammal's cell.

In certain embodiments, the invention provides a soluble construct comprising a FGF19 and/or FGF21 polypeptide that is capable of binding to and sequestering β-Klotho on the surface of a mammal's cell. In certain embodiments, the FGF21 polypeptide comprises the amino acid residues 169-209 of SEQ ID NO:3 ($FGF21_{CT}$). In other embodiments, the FGF19 polypeptide comprises the amino acid residues 170-216 of SEQ ID NO:2 ($FGF19_{CT}$). $FGF21_{CT}$ or $FGF19_{CT}$ can be fused with another polypeptide, such as but not limited to a stability enhancing domain, such as but not limited to albumin, thioredoxin, glutathione S-transferase (GST), or a Fc region of an antibody. In certain embodiments, $FGF21_{CT}$ or $FGF19_{CT}$ and the stability enhancing domain are linked through a polypeptide comprising about 1-18 amino acids, 1-17 amino acids, 1-16 amino acids, 1-15 amino acids, 1-14 amino acids, 1-13 amino acids, 1-12 amino acids, 1-11 amino acids, 1-10 amino acids, 1-9 amino acids, 1-8 amino acids, 1-7 amino acids, 1-6 amino acids, 1-5 amino acids, 1-4 amino acids, 1-3 amino acids, 1-2 amino acids, or a single amino acid.

In other embodiments, the invention provides a soluble construct comprising a β-Klotho polypeptide that is capable of binding to and sequestering FGF19 and/or FGF21. In certain embodiments, the β-Klotho polypeptide comprises the extracellular region of human β-Klotho (amino acid residues 53-983 of SEQ ID NO:1), or a fragment thereof. In other embodiments, the fragment of the extracellular region of human β-Klotho comprises the amino acid residues 379-942 of SEQ ID NO:1. The β-Klotho polypeptide can be fused with another polypeptide, such as but not limited to a stability enhancing domain, such as but not limited to albumin, thioredoxin, glutathione S-transferase (GST), or a Fc region of an antibody. In certain embodiments, the β-Klotho polypeptide and the stability enhancing domain are linked through a polypeptide comprising 1-18 amino acids, 1-17 amino acids, 1-16 amino acids, 1-15 amino acids, 1-14 amino acids, 1-13 amino acids, 1-12 amino acids, 1-11 amino acids, 1-10 amino acids, 1-9 amino acids, 1-8 amino acids, 1-7 amino acids, 1-6 amino acids, 1-5 amino acids, 1-4 amino acids, 1-3 amino acids, 1-2 amino acids, or a single amino acid.

In yet other embodiments, the invention provides a soluble construct comprising a β-Klotho polypeptide that is capable of binding to FGFRs. In certain embodiments, the β-Klotho polypeptide comprises the extracellular region of human β-Klotho (the amino acid residues 53-983 of SEQ ID NO:1), or a fragment thereof. In other embodiments, the fragment of the extracellular region of human β-Klotho comprises the amino acid residues 533-575 of SEQ ID NO:1. The β-Klotho polypeptide can be fused with another polypeptide, such as but not limited to a stability enhancing domain, such as but not limited to albumin, thioredoxin, glutathione S-transferase (GST), or a Fc region of an antibody. In certain embodiments, the β-Klotho polypeptide and the stability enhancing domain are linked through a polypeptide comprising 1-18 amino acids, 1-16 amino acids, 1-14 amino acids, 1-12 amino acids, 1-10 amino acids, 1-8 amino acids, 1-6 amino acids, 1-5 amino acids, 1-4 amino acids, 1-3 amino acids, 1-2 amino acids, or a single amino acid.

(b) The Invention Provides a Composition That Binds to β-Klotho More Tightly Than Wild-Type FGF19 and/or FGF21

In one aspect, the invention provides a soluble construct comprising a FGF19 and/or FGF21 polypeptide that binds to β-Klotho more tightly than wild-type FGF19 and/or FGF21. In certain embodiments, the FGF19 polypeptide has a mutation in its C-terminal domain. In certain embodiments, the FGF21 polypeptide has a mutation in its C-terminal domain, such as but not limited to residues V188, R203 and/or L194. In other embodiments, the mutation for the FGF21 polypeptide comprises V188. In yet other embodiments, the mutation for the FGF21 polypeptide comprises R203W. In yet other embodiments, the mutation for the FGF21 polypeptide comprises L194F. The FGF19 and/or FGF21 polypeptide can be fused with another polypeptide, such as but not limited to a stability enhancing domain, such as but not limited to albumin, thioredoxin, glutathione S-transferase, or a Fc region of an antibody. In certain embodiments, the FGF19 and/or FGF21 polypeptide and the stability enhancing domain are linked through a polypeptide comprising 1-18 amino acids, 1-16 amino acids, 1-14 amino acids, 1-12 amino acids, 1-10 amino acids, 1-8 amino acids, 1-6 amino acids, 1-5 amino acids, 1-4 amino acids, 1-3 amino acids, 1-2 amino acids, or a single amino acid.

The compounds included in the compositions of the invention can form salts with acids, and such salts are included in the present invention. In certain embodiments, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Methods

In one aspect, the invention includes a method of treating or preventing a disease or disorder in a subject in need thereof.

In certain embodiments, the method comprises administering to the subject a therapeutically effective amount of a construct that prevents or minimizes binding of FGF19 and/or FGF21 and/or FGFR to β-Klotho on the surface of a mammal's cell. Non-limiting examples of diseases or disorders treated or prevented by the method includes liver cancer and colon cancer.

In certain embodiments, the method comprises administering to the subject a therapeutically effective amount of a construct that binds more tightly than wild-type FGF19 and/or FGF21 to β-Klotho on the surface of a mammal's cell. Non-limiting examples of diseases or disorders treated or prevented by the method includes obesity, diabetes, pancreatitis, nonalcoholic fatty liver disease (NAFLD), and nonalcoholic steatohepatitis (NASH).

In certain embodiments, the construct comprises a recombinant peptide and/or an antibody, and combinations thereof. In other embodiments, the antibody comprises at least one antibody selected from the group consisting of a polyclonal antibody, monoclonal antibody, humanized antibody, synthetic antibody, heavy chain antibody, human antibody, biologically active fragment of an antibody, and combinations thereof. In yet other embodiments, the subject is a mammal. In yet other embodiments, the mammal is human. In yet other embodiments, the construct is administered by an administration route selected from the group consisting of inhalational, oral, rectal, vaginal, parenteral, intracranial, topical, transdermal, pulmonary, intranasal, buccal, ophthalmic, intrathecal, and intravenous.

In certain embodiments, the subject is further administered at least one additional drug that treats the disease and/or disorder. In other embodiments, the construct and the at least one additional drug are co-administered. In yet other embodiments, the construct and the at least one additional drug are co-formulated.

Combination Therapies

The compounds and compositions identified using the methods described here are useful in the methods of the invention in combination with one or more additional compounds useful for treating the diseases or disorders contemplated herein. These additional compounds may comprise compounds identified herein or compounds, e.g., commercially available compounds, known to treat, prevent, or reduce the symptoms of the diseases or disorders contemplated herein.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Formulations

The invention also encompasses the use of pharmaceutical compositions of the invention to practice the methods of the invention.

Such pharmaceutical compositions may be provided in a form suitable for administration to a subject, and may comprise one or more pharmaceutically acceptable carriers, one or more additional ingredients, or some combination of these. The compositions of the invention may comprise a physiologically acceptable salt, such as a compound contemplated within the invention in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, intracranial, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the patient either prior to or after the manifestation of symptoms associated with the disease or condition. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or condition in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, intracranial, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ Film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and assaying conditions with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

Unless otherwise noted, all starting materials were obtained from commercial suppliers and used without purification.

The following resources were used herein:

Antibodies: anti-FGFR1 antibody, rabbit polyclonal (Bae et al., 2009, Cell 138:514-524); anti-β-Klotho antibody, R&D Systems (Ref. AF5889); anti-phosphotyrosine 4G10, Millipore, D5-1050.

Bacterial and Virus Strains: BL21-Gold (DE3) competent cells, Agilent Technologies (Ref 230132).

Chemicals, Peptides, and Recombinant Proteins: DMEM, Thermo Fisher (Ref. 11965092); Fetal Bovine Serum, Thermo Fisher (Ref 10437-028); Penicillin-Streptomycin, Thermo Fisher (Ref 15140-122); Geneticin, G-418, AmericanBio (Ref. AB05058-00020); Lipofectamine 2000, Thermo Fisher (Ref. 11668019); Hygromycin B, Thermo Fisher (Ref 10687010); Complete protease inhibitor cocktail, Roche (Ref 11836145001); Swainsonine, Cayman Chemical (Ref. 16860); Kanamycin Sulfate, Americanbio (Ref. AB01100-00010); Ampicillin, Sodium salt, Americanbio (Ref. AB00115-00010); Isopropyl β-D-thiogalactopyranoside (IPTG), Americanbio (Ref. AB00841-00010); PEG 1,000, Hampton Research (Ref. HR2-523); PEG 4,000, Hampton Research (Ref. HR2-529).

Cell Lines: HEK293 EBNA, ATCC (Ref. CRL-10852); L6 myoblast expressing WT-FGFR1 (Bae et al., 2009, Cell 138:514-524); L6 myoblast expressing WT-FGFR1 (Bae et al., 2009, Cell 138:514-524).

Recombinant DNA: pCEP4 vector, Thermo Fisher (Ref. V04450); pBabe vector, AddGene; pET28b vector, Novagen (Ref 69864-3); pGEX-4T-1 vector, GE Healthcare (Ref 28-9545-49).

Software and Algorithms: HKL2000; Otwinowski & Minor, 1997, Methods Enzymol. 276:307-326 (www dot hklxray dot corn); XDS, Kabsch, 2010, Xds. Acta Crystallogr. D Biol. Crystallogr. 66:125-132 (xds dot mpimfheidelberg dot mpg dot de); Phenix, Adams et al., 2010, Acta Crystallogr. D Biol. Crystallogr. 66:213-221 (www dot phenixonline dot org); PHASER, McCoy et al., 2007, J. Appl. Crystallogr. 40:658-674 (www dot ccp4 dot ac dot uk); Coot, Emsley et al., 2010, Acta Crystallogr. D Biol. Crystallogr. 66:486-501 (www2 dot mrclmb dot cam dot ac dot uk/personal/pemsley/coot); PyMol, Schrödinger LLC (www dot pymol dot org); MO. Affinity Analysis, NanoTemper (Ref. MO-S001A).

Others: Hyperflask M, Corning (Ref 10030); EmultiFlex-C3, Avestin (Ref. EmultiFlex-C3); Ni-NTA agarose, Qiagen (Ref 30210); Glutathion Sepharose 4B, GE Healthcare (Ref 17-0756-01); Rec-Protein A-Sepharose 4B, Thermo Fisher (Ref 101142); Monolith NT.115Pico Instrument, NanoTemper (Ref. MO-G006); Mosquito Crystal, TTP Labtech (Ref. Mosquito Crystal); Rock Imager 1000, Formulatrix (Ref. Rock Imager 1000).

Plasmid Construction cDNA regions that encode for either the amino acid residues 30-983 (sKLB) of human β-Klotho (KLB) were amplified together with the tobacco etch virus (TEV) protease cleavage site and linker of four Gly residues. The resulting sequence was subcloned into a modified pCEP4 vector (Thermo Fisher Scientific Inc.), which contains sequence for Fc region of human IgG1. The expression vector for C-terminal HA-tagged KLB was generated by subcloning the gene of full-length KLB together with the HA-tag sequence into a pBABE vector. All plasmids of KLB mutants were generated by following standard site-directed mutagenesis protocol using a plasmid containing WT C-terminal HA-tagged KLB.

Protein Expression Using Mammalian Cell Expression System

HEK293-EBNA cells were cultured in a humidified incubator with 5% $CO_2$ at 37° C. in DMEM (Thermo Fisher Scientific Inc.) containing 10% Fetal Bovine Serum (FBS), 100 U/mL Penicillin-Streptomycin, and 250 µg/mL G-418. The plasmids were transfected into HEK293-EBNA cells with the Lipofectamine 2000 (Thermo Fisher Scientific Inc.) and selected by treatment with 200 µg/mL of Hygromycin B (Thermo Fisher Scientific Inc.) for 2-3 weeks. Cells stably expressing sKLB-Fc were expanded in Hyperflasks (Corning Inc.), and the media was changed to DMEM with 5% FBS when cell confluency had reached about 70%. After 7 days, the medium was collected after centrifugation at 5,000×g and filtration through 0.2 µm membrane. In addition, 15 µM swainsonine (Cayman Chemical) was added to the medium of cultured cells used for preparing proteins for crystallization.

Purification of sKLB and $KLB_{D1}$

Media harvested from the cells expressing sKLB-Fc were incubated with recombinant Protein A Sepharose 4B (Thermo Fisher Scientific Inc.) overnight at 4° C. The resin was washed with 50 column volumes of PBS and the protein was eluted from the resin using 0.1 M Glycine-HCl, pH 3.5 and immediately neutralized with 0.1 M Tris, pH 7.4. The eluted protein was incubated with recombinant TEV protease for 2 hours at room temperature to cleave the C-terminal Fc-tag, followed by incubation with recombinant Protein A Sepharose 4B for 30 min, at 4° C. to remove Fc-tag and undigested protein. The protein was then subjected to a cation exchange chromatography (Mono S 5/50 GL, GE Healthcare) using 20 mM sodium phosphate buffer at pH 7.0 (for sKLB) or at pH 6.5 (for $KLB_{D1}$) and purified using a linear salt gradient.

The elution fractions containing sKLB were pooled, concentrated, and subjected to Superdex 200 Increase 10/300 GL (GE Healthcare) size exclusion chromatography column pre-equilibrated with 20 mM HEPES, 150 mM NaCl, pH 7.0. The eluted fractions containing sKLB were pooled, concentrated, flash-frozen, and stored at −80° C. until further use. For crystallization of sKLB, two potential N-glycosylation sites, Asn308 and Asn611, were mutated to glutamine. The mutations were introduced to the sKLB-Fc plasmid by standard QuikChange site-directed mutagenesis. The expression and purification of mutant sKLB was identical to those used for WT sKLB.

Expression and Purification of Recombinant FGF21, GST-FGF21$_{CT}$, and FGFR1c$_{D2D3}$ DNA sequence that encodes for human FGF21 amino acid 29-209 harboring three mutations, L126R, P199G, and A208E, was codon-optimized for E. coli expression and synthesized (Blue Heron Biotech, LLC.). After cloning into a pET28a vector (Novagen), the plasmid was transformed into BL21-Gold (DE3) competent cells. Transformants were grown in LB medium containing 50 μg/mL kanamycin, shaking at 240 rpm at 37° C. When the $A_{600}$ of the samples reached 0.6, the bacteria were induced with 1 mM IPTG for 4 hours at 37° C. The bacterial cell pellet, collected by centrifugation at 5,000×g at 4° C., was lysed in 20 mM sodium phosphate buffer, 500 mM NaCl, 5% glycerol, at pH 7.8 using EmulsiFlex-C3 homogenizer (Avestin, Inc.), followed by centrifugation at 20,000×g for 30 min at 4° C. The supernatant containing N-terminal His6-tagged FGF21 was supplemented with 10 mM imidazole and incubated with Ni-NTA agarose (Qiagen) for 1 hr at 4° C. The resin was washed with 20 column volume of lysis buffer containing 10 mM imidazole, and the protein was eluted from the resin with lysis buffer containing 300 mM imidazole. The protein solution was injected into HiLoad 26/600 Superdex 200 (GE Healthcare) size exclusion chromatography column equilibrated with 20 mM HEPES, 900 mM NaCl at pH 7.5. The eluted fractions containing FGF21 were pooled, concentrated to about 1.5 mg/mL, flash-frozen, and stored at −80° C. until further study.

For generating GST-FGF21$_{CT}$, DNA sequence encoding the amino acid residues 169-209 of FGF21 was cloned into pGEX-4T-1 vector (GE Healthcare), and the plasmid was transformed into BL21-Gold (DE3) competent cells (Agilent Technologies). Transformants were grown in LB media containing 100 μg/mL ampicillin at 37° C. until $A_{600}$ reached 0.6, and induced with 1 mM IPTG for 4 hours at 37° C. Bacteria cells were collected, lysed in PBS using EmulsiFlex-C3 homogenizer (Avestin, Inc.), and centrifuged at 20,000×g for 30 minutes at 4° C. The supernatant containing GST-FGF21$_{CT}$ was incubated with Glutathione Sepharose 4B (GE Healthcare) pre-equilibrated with PBS, for 1 hour at 4° C. The beads were washed with 50 column volume of PBS and the protein was eluted with 20 mM HEPES, 150 mM NaCl, 10 mM reduced glutathione, pH 7.3. The protein solution containing GST-FGF21$_{CT}$ was then dialyzed against 20 mM HEPES, 150 mM NaCl before flash-freezing and storage at −80° C. A peptide corresponding to the C-terminal region of FGF21 containing the amino acid residues 174-209 with two substitutions, P199G and A208E, FGF21$_{CT}$ was synthesized and purified by the Tufts University Core Facility. The ligand binding region of FGFR1c was expressed in E. coli as an insoluble fraction. The protein was refolded and purified as previously described (Plotnikov et al., 2000, Cell 101:413-424).

Crystallization, X-ray Diffraction Data Collection, and Structure Determination sKLB gave rod-shaped crystals when mixed with equal volume of well solution containing 14% PEG4000, 0.1 M MES, pH 6.0 and equilibrated for 10-15 days using the hanging drop vapor diffusion method. The crystals were cryopreserved by gradually transferring crystals to the mother liquor supplemented with 30% glucose before being flash-frozen in liquid nitrogen. For sKLB in complex with FGF21$_{CT}$, FGF21$_{CT}$ was dissolved in 14% PEG4000, 0.1 M MES, pH 6.0 and added to the drop that contains sKLB crystals. Addition of FGF21$_{CT}$ immediately caused deformation in most of the crystals.

Crystals that stayed intact were gradually transferred into the artificial mother liquor, supplemented with 30% glucose and 50 μM FGF21$_{CT}$ before being flash-frozen in liquid nitrogen. X-ray diffraction data was collected at the beamlines BL-14 at the Stanford Synchrotron Radiation Lightsource, SLAC National Accelerator Laboratory, CA (for sKLB) and 24-ID-E at the Advanced Photon Source, Argonne, Ill. (for sKLB in complex with FGF21$_{CT}$). The diffraction data sets were processed using HKL2000 (Otwinowski & Minor, 1997, Methods Enzymol. 276:307-326) and XDS (Kabsch, 2010, Xds. Acta Crystallogr. D Biol. Crystallogr. 66:125-132). Initial phases for the data set for KLB were calculated by molecular replacement with PHASER (McCoy et al., 2007, J. Appl. Crystallogr. 40:658-674).

Refinement was iteratively performed using PHENIX (Adams et al., 2010, Acta Crystallogr. D Biol. Crystallogr. 66:213-221) followed by manual model building using COOT (Emsley et al., 2010, Acta Crystallogr. D Biol. Crystallogr. 66:486-501). As for the data set for sKLB in complex with FGF21$_{CT}$, initial phase information was obtained by molecular replacement using the final coordinates of sKLB. Iterative cycles of refinement and rebuilding of sKLB model improved the phase, resulting significant electron densities for FGF21$_{CT}$. Subsequently, the model for FGF21$_{CT}$ was manually built based on the $|F_o|-|F_c|$ map followed by the final refinement cycles. All the figures containing the structures were generated using the PyMOL Molecular Graphics System, Version 1.8 (Schrödinger, LLC.).

MicroScale Thermophoresis (MST) Measurements

All MST measurements were performed using the Monolith NT.115Pico instrument (NanoTemper Technologies) with Monolith NT.115 MST Premium Coated Capillaries. Purified FGF21 was fluorescently labeled using the Monolith Protein Labeling Kit RED-NHS (NanoTemper Technologies) according to the instruction provided by the manufacturer. Samples for binding affinity measurements of FGF21 to sKLB were prepared by mixing 35 nM of fluorescently labeled FGF21 (fl-FGF21) with a series of concentrations, ranging from 0.03 nM to 1000 nM, of purified sKLB in 20 mM HEPES, 150 mM NaCl, pH 7.0, 0.05% Tween-20, 1 mg/mL BSA. The thermophoretic movements of fl-FGF21 in each samples were monitored (LED 20%, IR laser 20%) and the normalized fluorescence intensities ($F_{Norm}$), defined as $F_{hot}/F_{cold}$ (where $F_{cold}$ and $F_{hot}$ refer to the fluorescence intensities averaged over is period before IR laser is on and 29 s after IR laser is on, respectively), for each samples were plotted against the concentrations of sKLB. For the competition assays, the thermophoresis of fl-FGF21 was measured for samples where the concentration of fl-FGF21 and sKLB mixture was kept constant with the concentrations of GST-FGF21$_{CT}$ varying from 2.1 nM to 35000 nM. All the data were analyzed with the MO Affinity Analysis software (NanoTemper Technologies) provided by the manufacturer.

Cell-based Activity Assays

L6 cells stably co-expressing WT FGFR1c together with either WT β-Klotho or a variety of β-Klotho mutants, were grown in DMEM supplemented with 10% FBS, 100 U/mL Penicillin-Streptomycin, 0.1 mg/ml hygromycin and 1 µg/ml puromycin. Cells were starved overnight in DMEM with 0.5% FBS and stimulated for 10 minutes at 37° C. with either FGF1 or FGF21 at concentrations of 5 nM and 25 nM, respectively. Cells were then lysed and subjected to immunoprecipitation with anti-FGFR1 antibody followed by SDS-PAGE. The samples were then subjected to immunoblotting with either anti-phosphotyrosine (pTyr), anti-β-Klotho or anti-FGFR1 antibodies.

Quantification and Statistical Analysis

Each binding affinity measurements was performed three times using independent samples.

Example 1: Structure of β-Klotho Extracellular Region

The overall structure of sKLB features two tandem GH domains; D1 (the amino acid residues 53-507) and D2 (the amino acid residues 521-968), which are connected by an unstructured and flexible linker (FIG. 1A). Four loop regions in the structure of sKLB containing potential N-glycosylation sites could not be modeled due to poor electron density: a loop between H0 and S1 (residues 63-73), a loop between H1b and H1c (residues 119-125), a loop between S9 and H9a (residues 538-574), and the C-terminus (residues 968-983) of the protein. With the exception of the C-terminus, these loops are depicted in the sKLB structures as dashed lines (FIG. 1A).

Superimposing the structure of human cytosolic β-glucosidase (PDB: 2ZOX) on the structures of each of the two GH domains in sKLB domains gives Cα RMSDs of 1.08 Å for D1 and 1.39 Å for D2 (Krissinel & Henrick, 2004, Acta Crystallogr. D Biol. Crystallogr. 60:2256-2268), demonstrating the strong similarity of both D1 and D2 the glycoside hydrolase family-1 (GH1) of enzymes (FIGS. 2A-2E). The GH1 family of proteins are typically enzymes that hydrolyze glycosidic linkages between carbohydrate moieties through a double-replacement mechanism mediated by two conserved glutamates located in their active site. One of the two catalytic glutamates is replaced by another amino acid in each of the sKLB domains (FIGS. 2C-2E). The first glutamate in D1 is replaced by N241, whereas the second glutamate in D2 is replaced by A889, indicating that neither GH domain in β-Klotho can function as an active glycoside-hydrolase enzyme. Each GH domain has either lost its nucleophilic residue (in D2) or the acid/base catalyst (in D1), making D1 a bona fide pseudo-glycosidase, but allowing the possibility that D1 might retain ability to form covalent intermediates with specific substrates as seen with in PDB ID 2ZOX when the acid/base glutamate was replaced by glutamine. Structural alignment using the Dali server (Holm & Rosenstrom, 2010, Nucleic Acids Res. 38:W545-549) indicates that GH1 and GH5 members exhibit high structural similarities to each of the GH domains of sKLB, implying a common evolutionary origin.

Although the overall structures of the GH domains in sKLB are very similar to GH1 family enzymes, the two sKLB GH domains exhibit important structural features that set them apart from the GH1 family of enzymes.

D1 pseudo-substrate binding pocket. In addition to having one of the two glutamates required for enzymatic activity replaced by an asparagine as described elsewhere herein, the pocket in D1 that corresponds to the substrate-binding region in GH1 family enzymes is largely occluded by a short helix, H6a (FIGS. 2A and 9B). Moreover, a helix-turn-strand element (H6a-turn-S6b) in this region, specific to β-Klotho D1 (green in FIG. 2A), provides part of the FGF21 binding site and is quite distinct from the strand-helix-strand element (grey in FIG. 2A) in corresponding regions of cytosolic β-glucosidase. Other features unique to β-Klotho include a short helix, H0 (FIG. 2A), which begins with the first amino acid following the sKLB signal sequence (F53). This helix interacts with H5a, H6b and S5b, mostly through hydrophobic interactions, and precedes a disordered loop that is followed by the core structural elements of the $(β/α)_8$ fold. E416, the remaining "catalytic" residue in D1 is located at the bottom of the substrate binding pocket and the orientation of the side chain of E416 is identical to the orientation of the side chain of the corresponding nucleophilic E373 residue of human cytosolic β-glucosidase.

D2 pseudo-substrate binding pocket. The pocket in D2 that corresponds to the substrate binding pocket in GH1 family enzymes is not occluded by an alpha-helix in the D2 domain, but is instead accessible and occupied by a MES molecule from the crystallization buffers. The morpholine ring of MES interacts with aromatic rings from three phenylalanines, F931, F826, and F942, which also play a role in the interaction of sKLB with its ligands. The D2 pocket is accessible in part because of the existence of a disordered region between S9 and H9a (the amino acid residues 538-574), resulting in formation of a more groove-like feature in this domain rather than the pocket that accommodates substrate in the active site of GH1 family members. The amino acid sequence and the length of this region vary significantly among GH1 family members. Furthermore, limited proteolysis of sKLB yields two fragments of approximately 75 and 50 kDa that cannot be separated by any attempted purification methods. N-terminal sequence analysis of the two degradation products indicated that the cleavage sites lie within the disordered region between S9 and H9a.

Example 2: Structure of sKLB in Complex with FGF21$_{CT}$

The C-terminal tails (CT) of FGF19 and FGF21 bind to β-Klotho, whereas the CT of FGF23 binds to α-Klotho. Various experimental approaches were used to confirm that FGF21$_{CT}$ binds to sKLB, and quantitative binding studies were employed to establish that the dissociation constant ($K_D$) for this binding is 43 nM. This high-affinity binding of FGF21$_{CT}$ to sKLB prompted determination of the crystal structure of sKLB bound to FGF21$_{CT}$. An FGF21$_{CT}$ peptide corresponding to FGF21 amino acids 175-209 was synthesized with P199G and A208E mutations to prevent degradation. The peptide was soaked into crystals of the sKLB:Nb914 complex, and diffraction data were collected to 2.6 Å resolution.

Figure 3A:
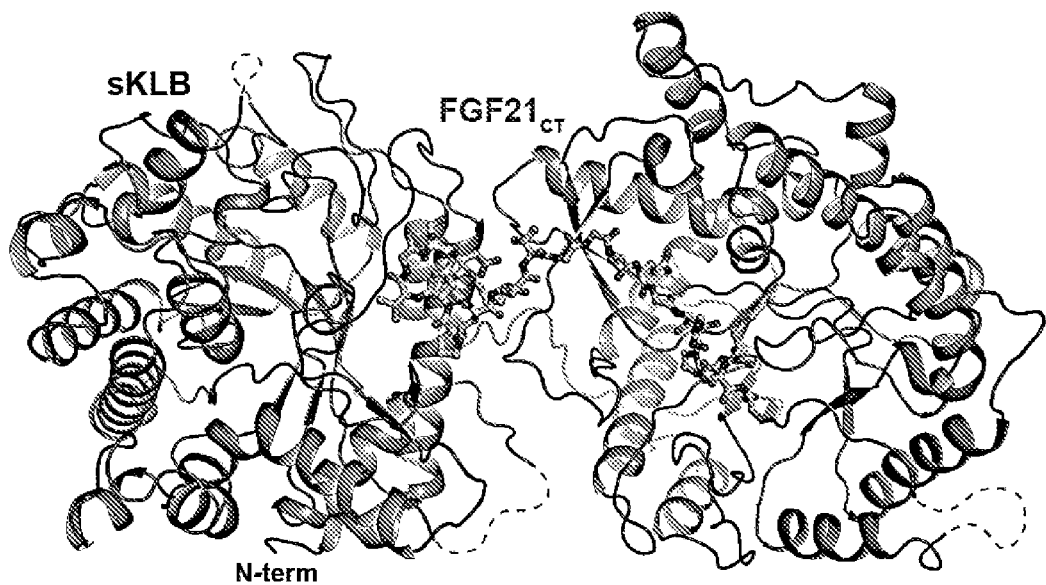
FIGS. 3A-3E illustrate an exemplary crystal structure of sKLB bound to FGF21$_{CT}$, and interactions between sKLB and FGF21$_{CT}$. The structure of sKLB (green) in complex with FGF21$_{CT}$ (salmon) is shown as ribbon and ball-and-stick representation (FIG. 3A), and surface representation (FIG. 3B). Regions that do not exhibit significant electron densities are shown as grey dashed lines.
Figure 3B:
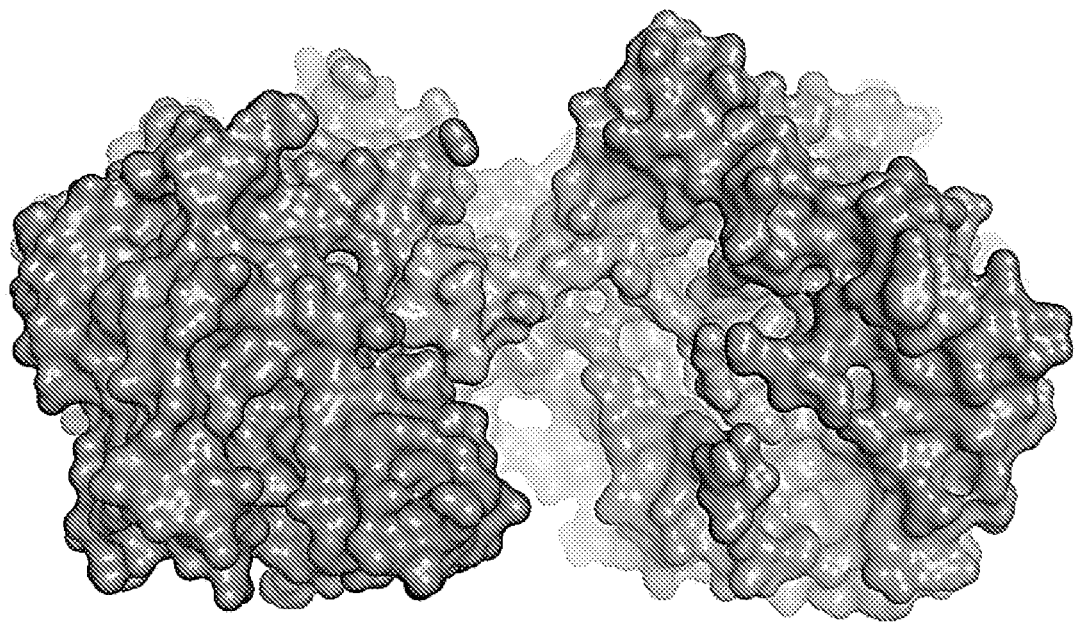
Figure 3C:
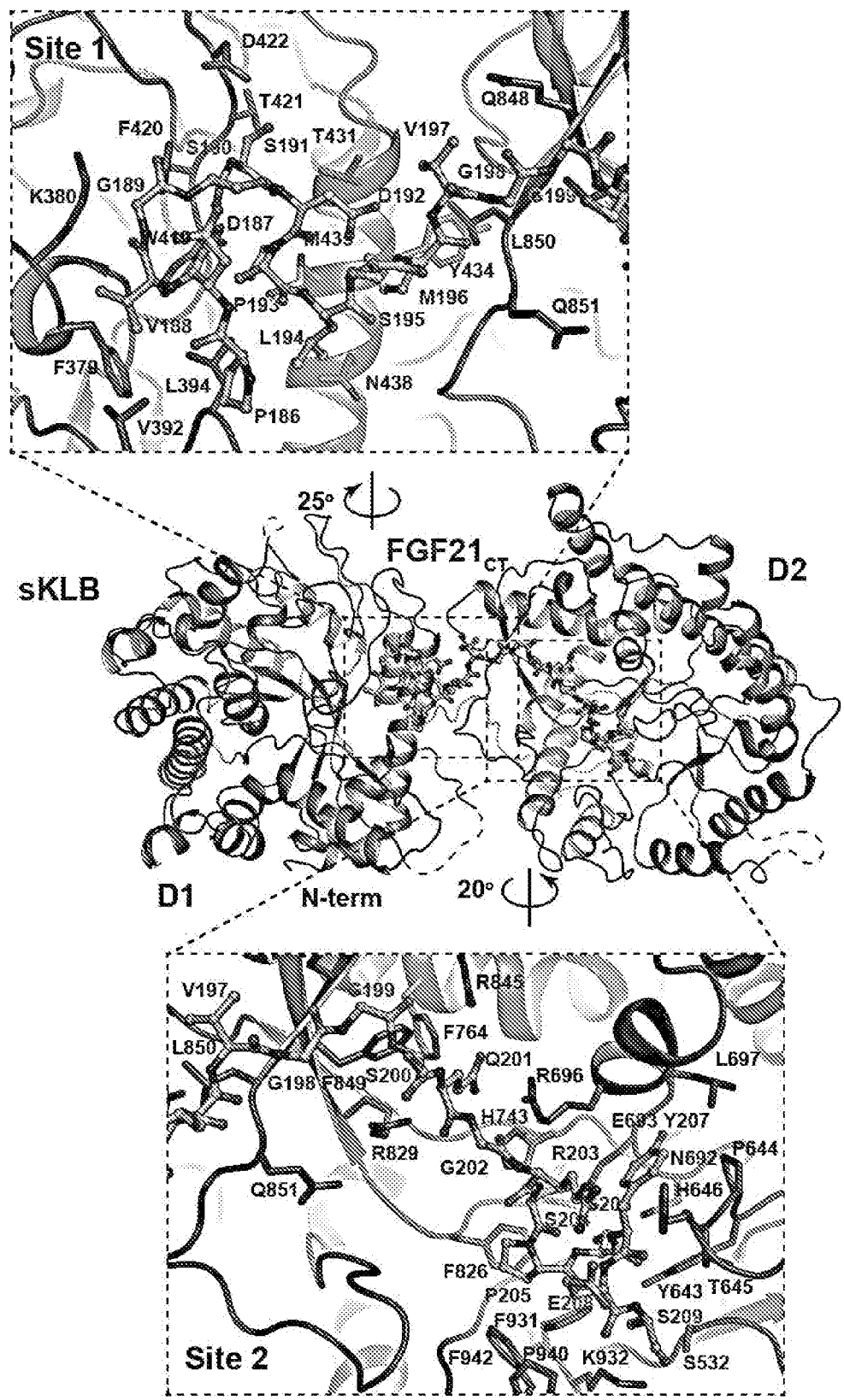
Figure 3D:
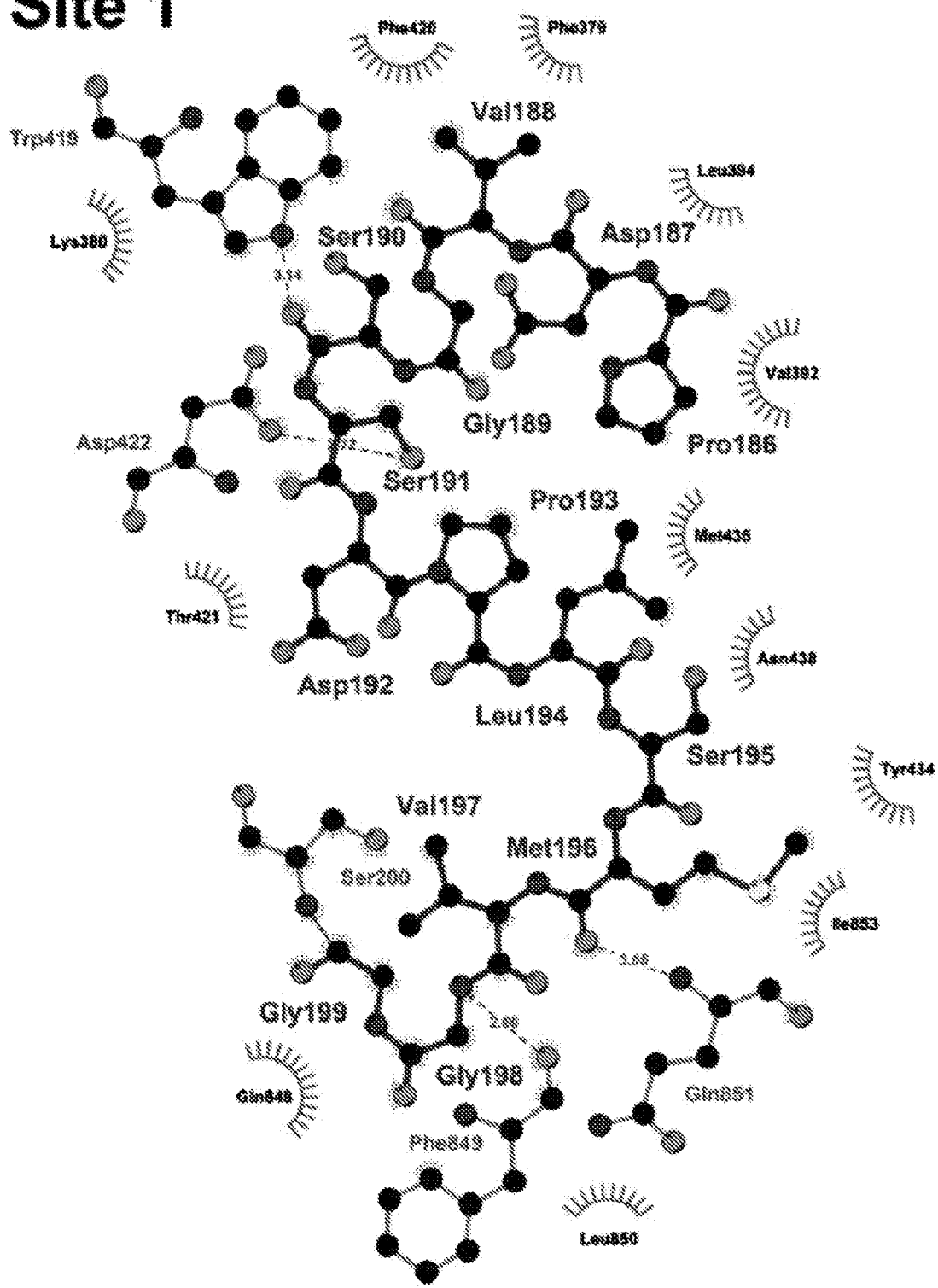
Figure 3E:
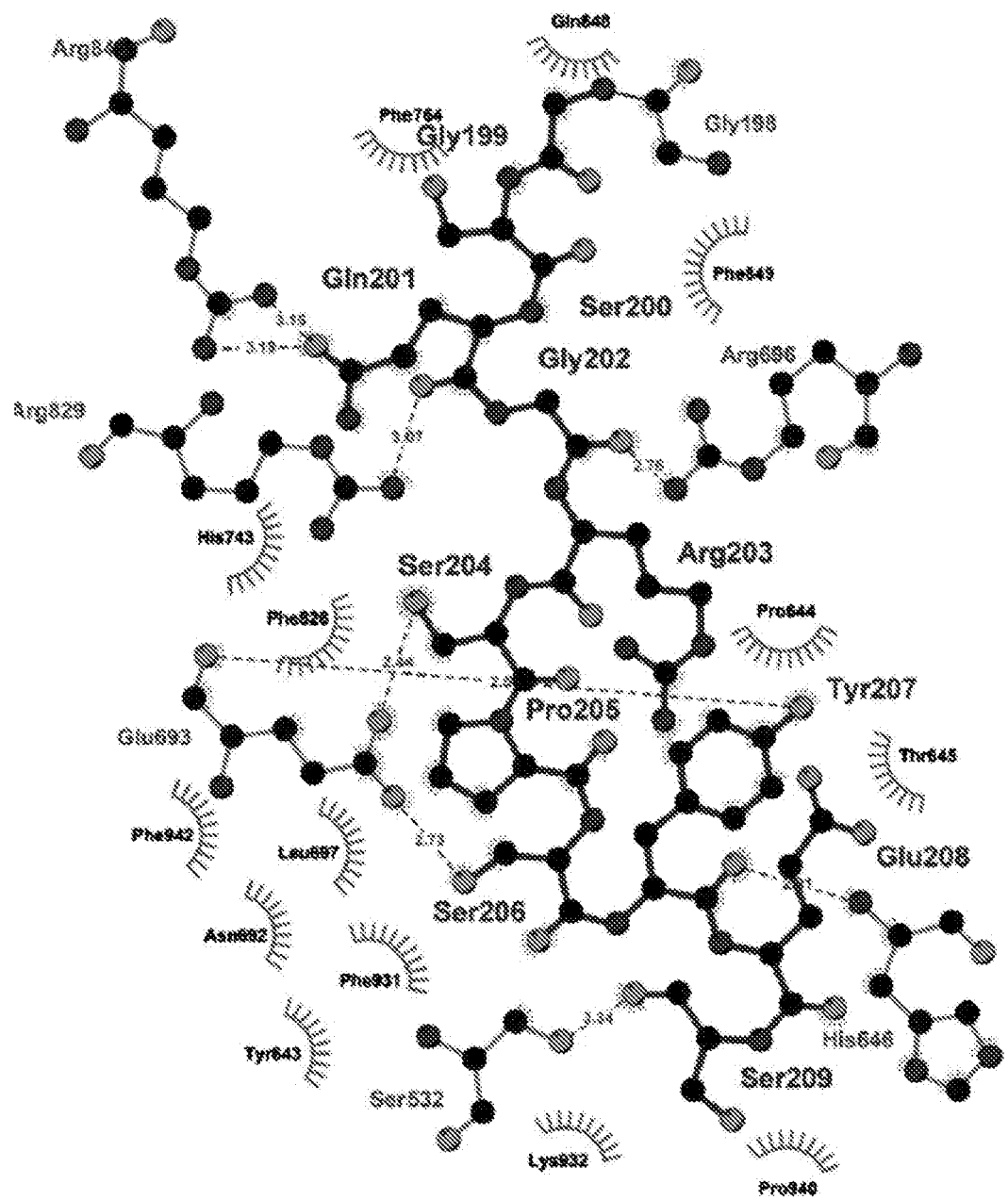

The structure was solved by molecular replacement using the structure of sKLB as a search model (FIGS. 3A-3E), and exhibited clear electron density corresponding to the FGF21$_{CT}$ peptide lying across the middle of sKLB. After refinement, the final model (with $R_{work}/R_{free}$ of 0.19/0.23) contains amino acids P186 to S209 from FGF21$_{CT}$ bound to sKLB (FIGS. 13C-3E). FGF21$_{CT}$ binds to an elongated interface that spans D1 and D2 of sKLB, with no influence on the structure of either individual domain as judged by α-carbon RMSDs of 0.33 and 0.49 Å for D1 and D2 respectively when overlaid on the unliganded sKLB structure. The FGF21$_{CT}$:sKLB structure shows two distinct binding sites for two different regions of the peptide. One (site 1) is located on sKLB D1, and the other (site 2) is located in D2. The distance between the centers of the two sites is about 30 Å.

Figure 4A:
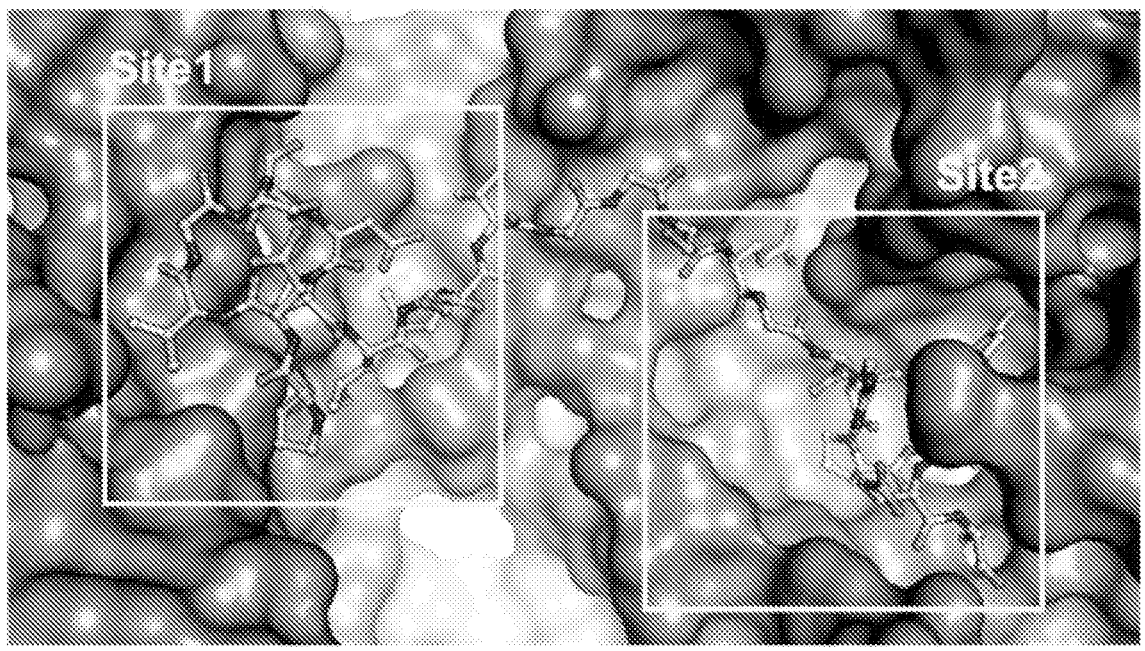
FIGS. 4A-4C illustrate two exemplary distinct FGF21 binding sites on β-Klotho.
Figure 4B:
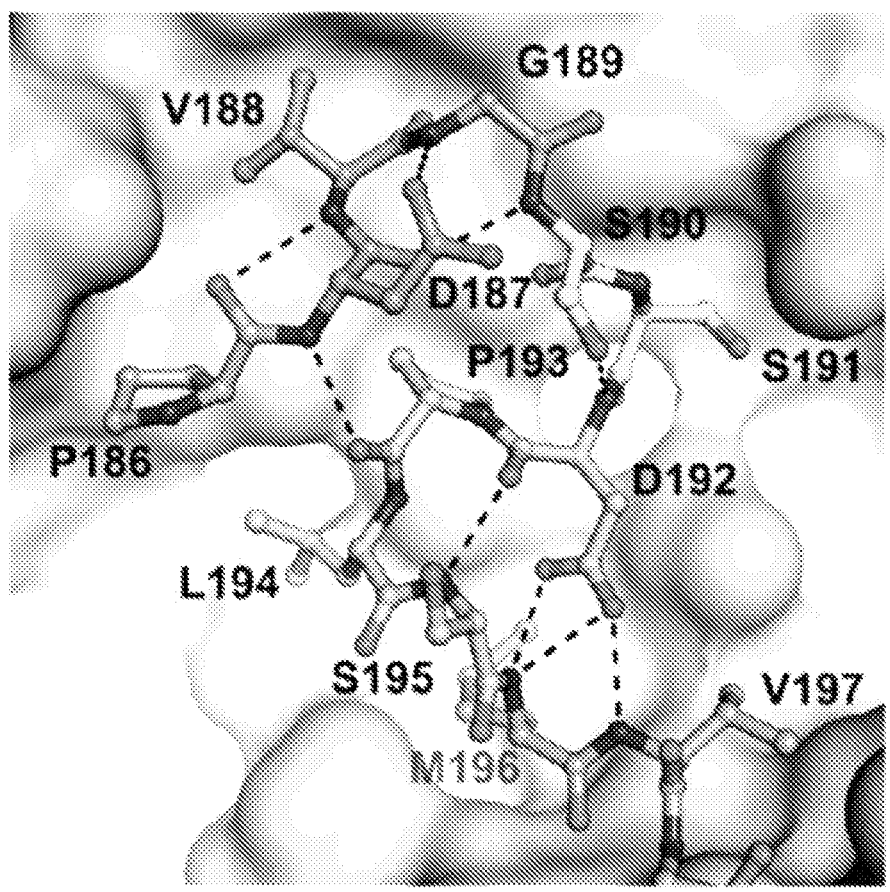

FGF21$_{CT}$ binding to Site 1. Site 1 on sKLB D1 engages amino acids P186-V197 of FGF21$_{CT}$, primarily through hydrophobic interactions (FIGS. 3D and 4B). Site 1 involves a surface created on D1 by H6a, H7, the loop between S6b and H6b, and the loop between S7 and H7. Most strikingly, the region of the bound peptide ligand that associates with site 1 adopts an unusually compact and rigid structure through the formation of several well-defined turns (FIG. 4B), as follows:

D187-V188-G189-S190 form a type I β-turn (orange in FIG. 4B) through hydrogen bonding of the carboxyl oxygen of D187 with the backbone nitrogen of G189 and of the backbone carbonyl of D176 with the backbone amide of S190.

S190-S191-D192 form an ST turn (yellow in FIG. 4B) through hydrogen bonding of the S190 hydroxyl with the backbone amide of D192.

D192-P193-L194-S195 (light blue in FIG. 4B) form a type β-turn (or an Asx turn that resembles a Schellman loop) through hydrogen bonding of the side chain carboxyl of D192 with the M196 and V197 backbone amides and of the D192 backbone carbonyl with the backbone amide of S195.

These consecutive turns also support a long-range hydrogen bond between the D187 backbone amide and the P193 carbonyl. These intramolecular interactions cooperate to form a well-defined structural element that makes multiple specific contacts with sKLB, burying a relatively large surface area of 606 Å$^2$. For this part of the FGF21$_{CT}$:sKLB interaction, the FGF21 amino acid sequence appears to define a structural element that docks onto the D1 surface close to where D1 and D2 interact.

Figure 4C:
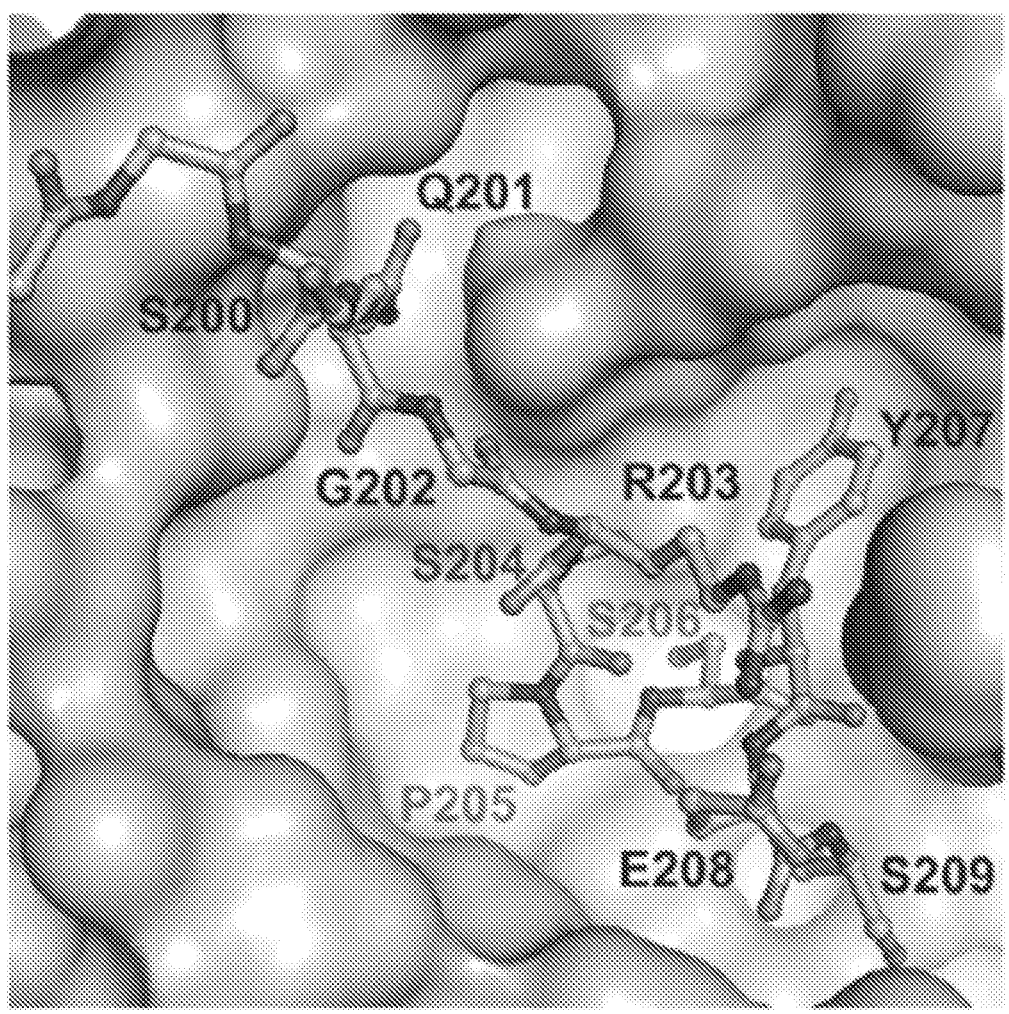
Figure 5A:
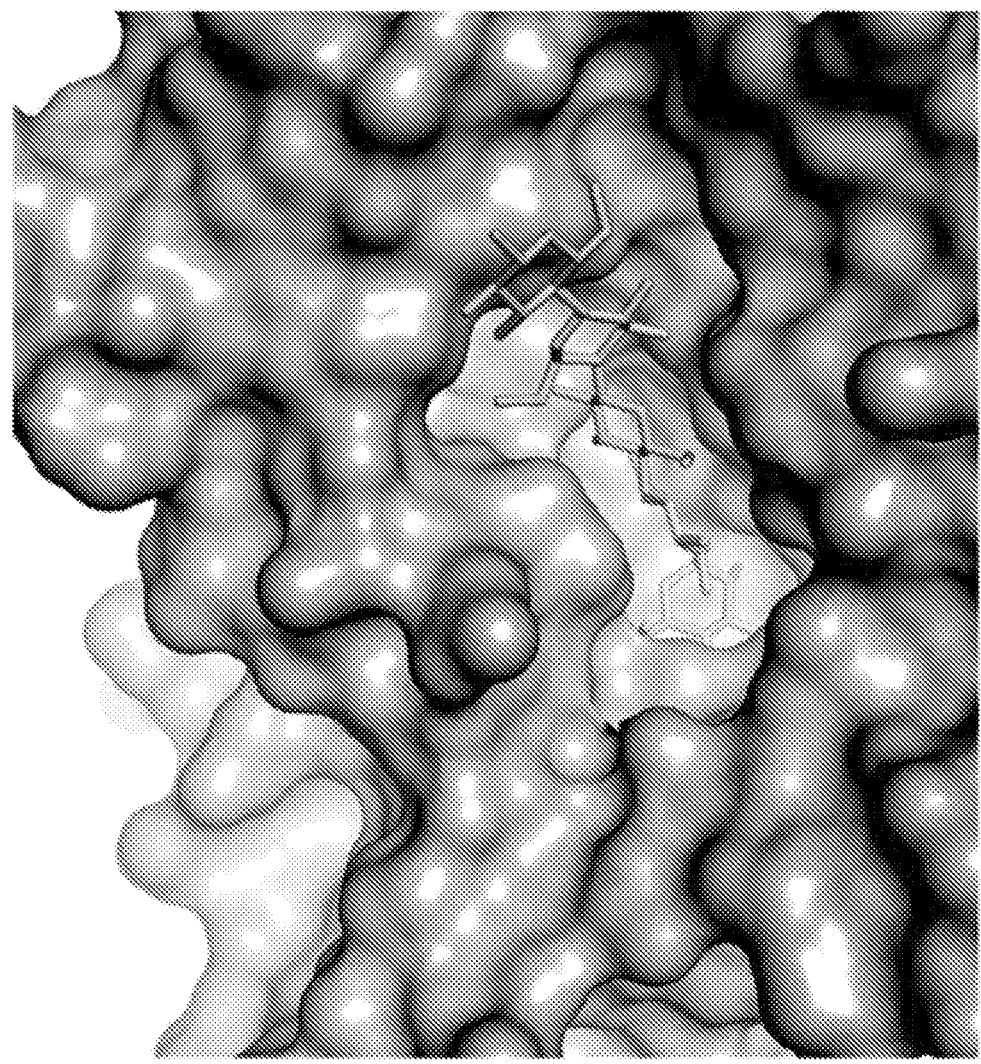
FIGS. 5A-5E illustrate an exemplary evolution of β-glucosidase into β-Klotho. The structures of (FIG. 5A) rice β-glucosidase (light blue, surface presentation) in complex with cellopentaose (orange, stick presentation) (PDB: 3F5K) and (FIG. 5B) site 2 of sKLB (pale green, surface presentation) in complex with FGF21$_{CT}$ (red, stick representation). Cellopentaose binds to the active site of β-glucosidase and FGF21$_{CT}$ binds to the corresponding pseudo-substrate binding site of β-Klotho.
Figure 5B:
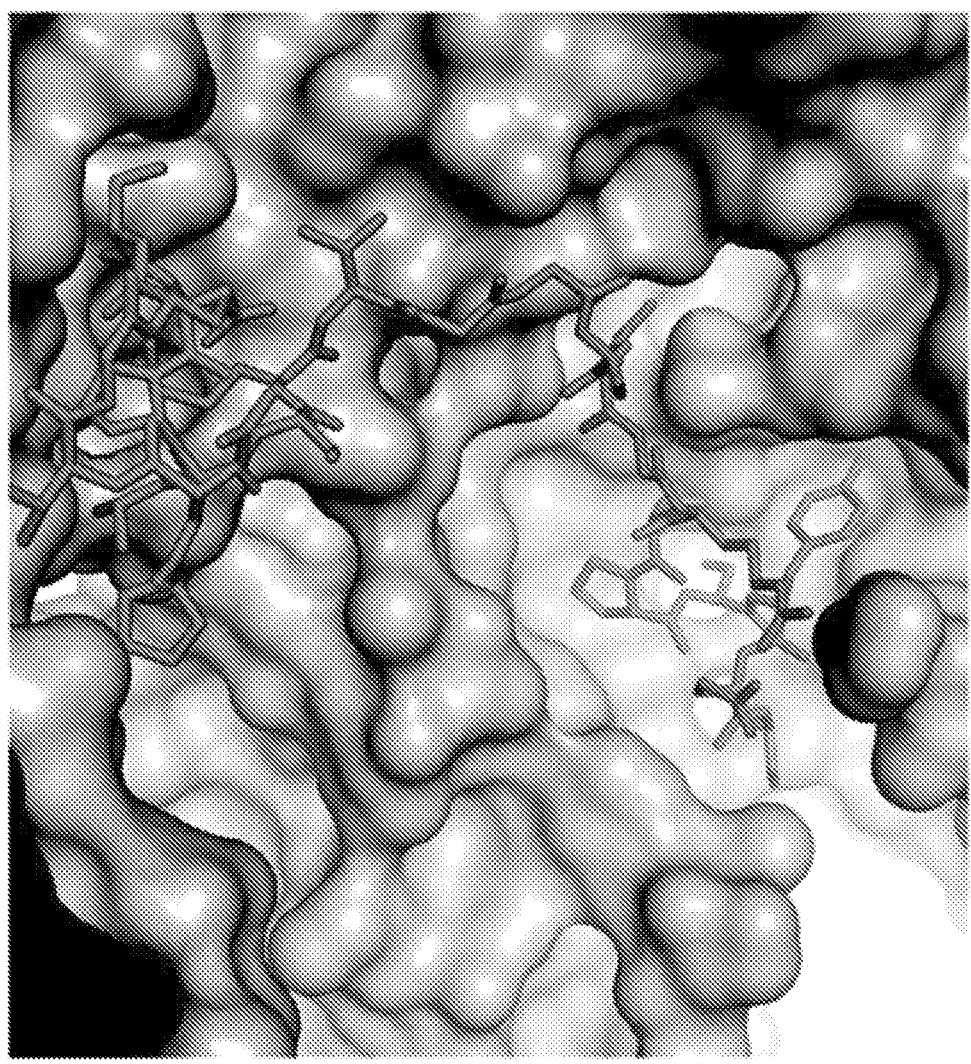
Figure 5C:
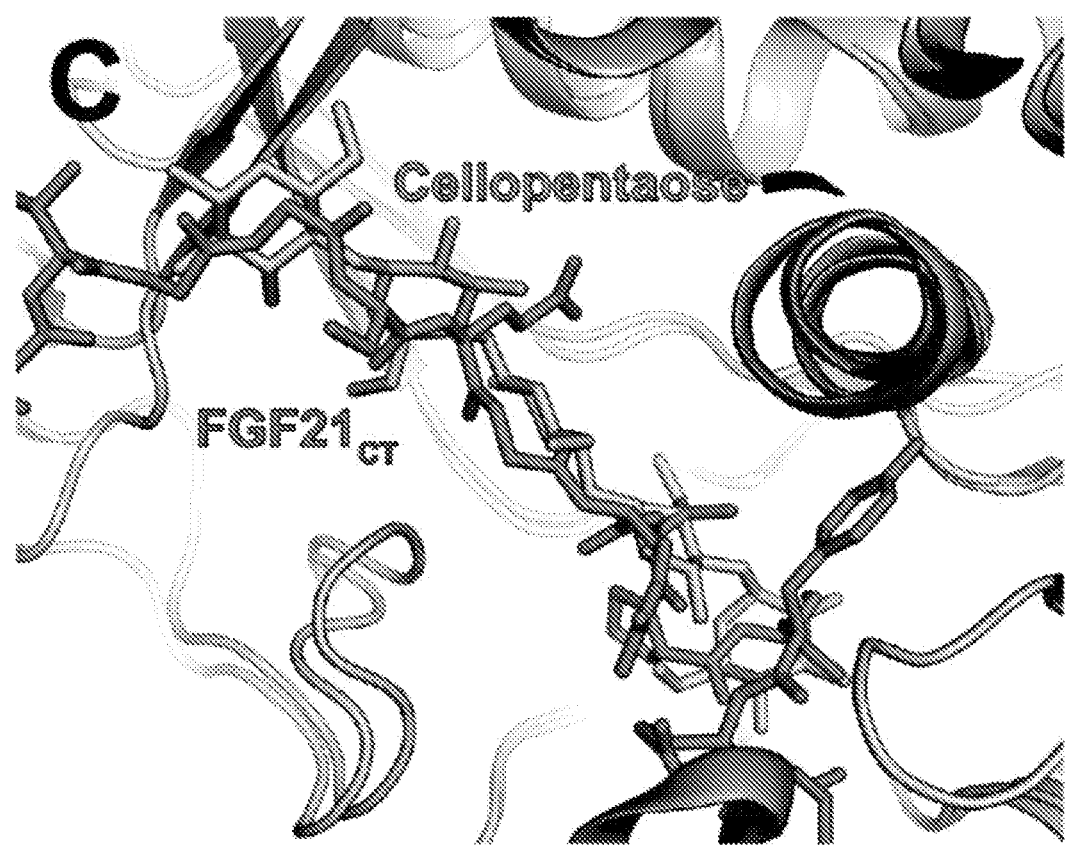
Figure 5D:
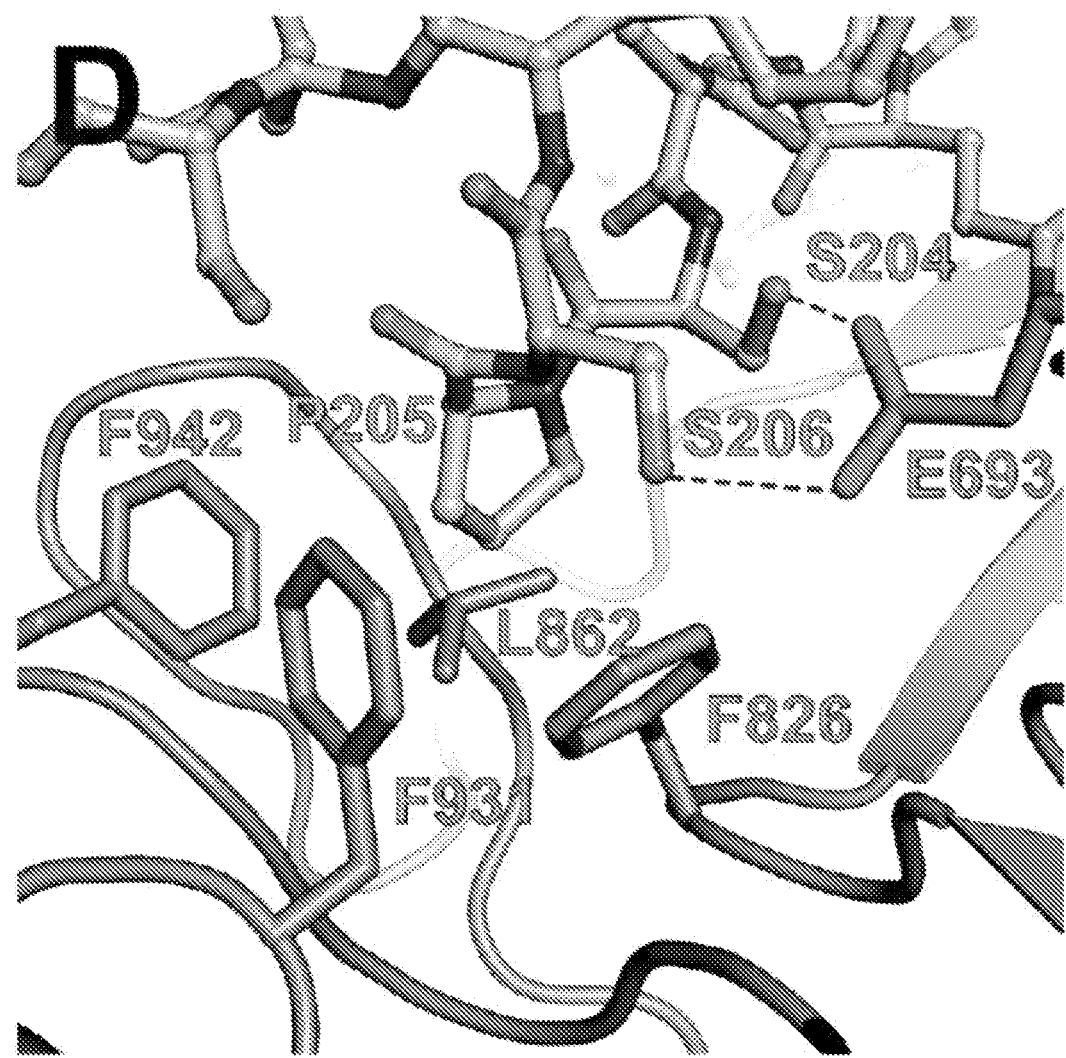

FGF21$_{CT}$ binding to Site2. The nature of the site 2 interactions contrasts starkly with site 1, comprising a network of inter-molecular interactions of the sort typically observed between proteins and short peptides (FIG. 4C). The individual interactions are summarized in the Ligplot figure shown in FIG. 3D-3E. However, residues 200-209 of the FGF21$_{CT}$ peptide project into what would be the substrate binding site occupied by glycosides that D2 of sKLB would hydrolyze if it were an active GH1 enzyme (FIGS. 5A-5E). The sequence (S-Q-G-R-S-P-S-Y-A-S), corresponding to residues 200-209 of FGF21$_{CT}$ of SEQ ID NO:3, is rich (50%) in residues with side-chain hydroxyl groups, suggesting the possibility that this region of FGF21 may indeed mimic a glycoside substrate. Given these characteristics, a feature of site 2 is the interaction between the side-chain carboxyl group of E693 in sKLB with hydroxyl groups of both S204 and S206 in FGF21$_{CT}$ (FIG. 5D). E693 corresponds to one of the two conserved "catalytic" glutamates, and would function as a general acid/base catalyst in the Koshland double-displacement reaction of glycoside hydrolases (whereas the potential nucleophilic glutamate is replaced by alanine in D2).

Amino acids 198-200 of FGF21$_{CT}$, which connect the ligand binding regions for site 1 and site 2, do not make significant contacts with sKLB. As this region of FGF21 is flexible and potentially accessible for proteolysis even when FGF21 is bound to sKLB, in a non-limiting embodiment cleavage between the site 1 and site 2 binding regions could represent a mechanism of termination of FGF21 signaling by targeted proteolysis.

Figure 5E:
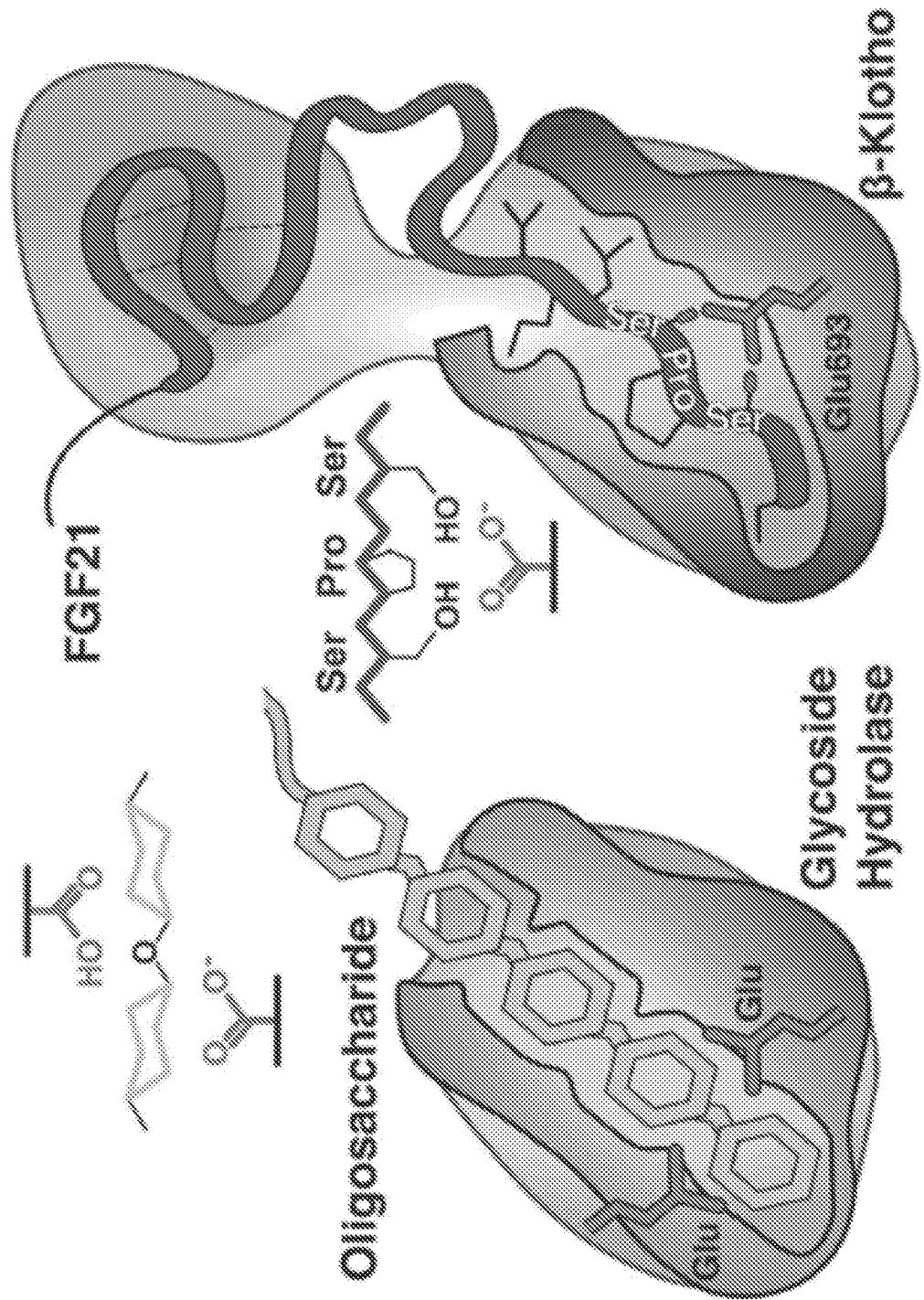

Example 3: Evolution of an Enzyme with Glycoside Hydrolase Activity Into a Receptor for Endocrine FGFs The crystal structure of sKLB bound to FGF21$_{CT}$ reveals how the basic framework of a glycoside hydrolase has evolved to become a specific receptor for endocrine FGFs. The β-glucosidase family of glycoside hydrolases catalyzes the hydrolysis of disaccharides as well as longer oligosaccharides, and several crystal structures of β-glucosidases in complex with oligosaccharide substrates such as cellotetraose (*P. polymyxa* BglB, PDB: 2Z1S) or cellopentaose (*O. sativa* BGlu1, PDB: 3F5K) have been determined. Superimposition of the crystal structures of substrate-bound β-glucosidases with the structure of sKLB in complex with FGF21$_{CT}$ shows that the backbone of residues 200-209 from FGF21$_{CT}$ aligns well with the location of oligosaccharides that occupy the catalytic pocket of β-glucosidases (FIGS. 5A-5C). As mentioned elsewhere herein, the mode of interaction between the hydroxyls of S204 and S206 from FGF21$_{CT}$ and the catalytic glutamate in D2 of sKLB, together with the hydrophobic interactions involving the P205, are highly reminiscent of substrate interactions seen for the glycoside hydrolases suggesting that this is a pseudo-substrate like interaction (FIG. 5D). Oligosaccharide substrates bound to this catalytic glutamic acid in β-glucosidases active sites lie in precisely the same position as the S204-P205-S206 motif of FGF21 bound to site 2 of sKLB. In addition, the residues in sKLB that form hydrophobic interactions with P205 of FGF21, i.e., F826, F931, and F942, align well with the corresponding hydrophobic residues in β-glucosidases. These unexpected similarities indicate that the substrate-binding region of glycoside hydrolases evolved to recognize a sugar mimicking S—P—S motif in FGF21 (FIG. 5E). FGF19 binds specifically to β-Klotho, and contains a S211-P212-S213 motif at its C-terminus, whereas FGF23 (which does not bind to β-Klotho) has no such sequence.

Figure 6A:
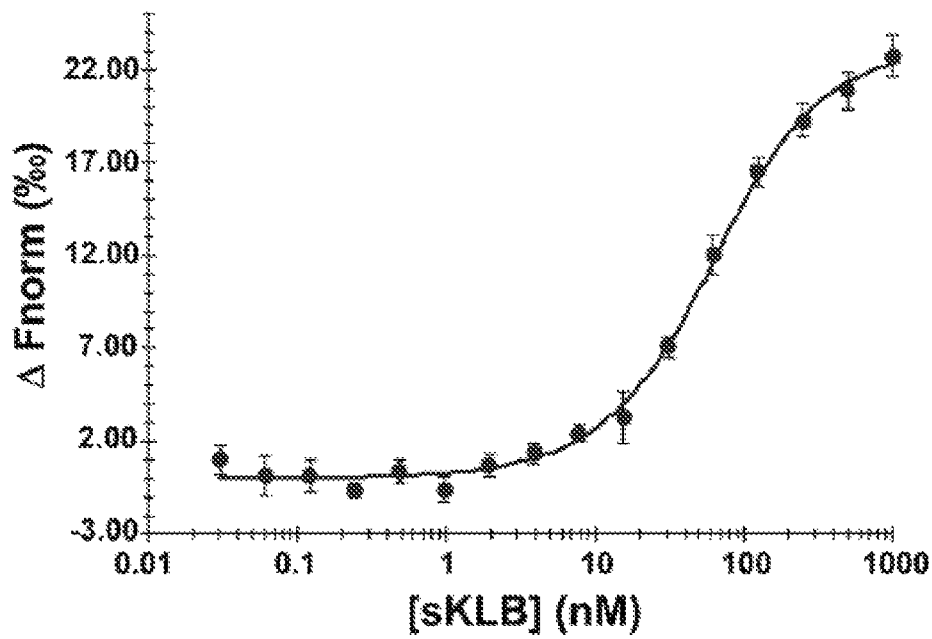
FIGS. 6A-6G illustrate an exemplary validation of FGF21 binding interface to β-Klotho by ligand binding and cell stimulation experiments. MST-based binding affinity measurements of (FIG. 6A) FGF21 and sKLB, and (FIG. 6B) FGFR1c$_{D2D3}$ and sKLB, yielding $K_D$=43.5±5.0 nM and $K_D$=940±176 nM, respectively. MST-based competition assay with GST-FGF21$_{CT}$ containing mutations in either (FIG. 6C) site 1-interacting region or (FIG. 6D) site 2-interacting region. IC$_{50}$ values for WT, 704±96 nM; D192A, 15900±6210 nM; P193A, 7160±2350 nM; S204A, 5990±1040 nM; S206A, 5560±1590.1 nM; Y207A, 6630±1570 nM. The error bars of each point represent variations of ΔFnorm (n=3).

Example 4: High-Affinity Pairwise Formation of FGF21/sKLB and sKLB/FGFR1, but not FGF21/FGFR1 Complexes The affinity of FGF21 for sKLB was measured using MicroScale Thermophoresis or MST (Seidel et al., 2013, methods 59:301-315), where the thermophoretic movement of fluorescently-labeled FGF21 (fl-FGF21) in solution is monitored upon sKLB binding. Fitting the normalized fluorescence intensities yields a dissociation constant ($K_D$) of 43.5 nM for FGF21 binding to sKLB (FIG. 6A).

Figure 6B:
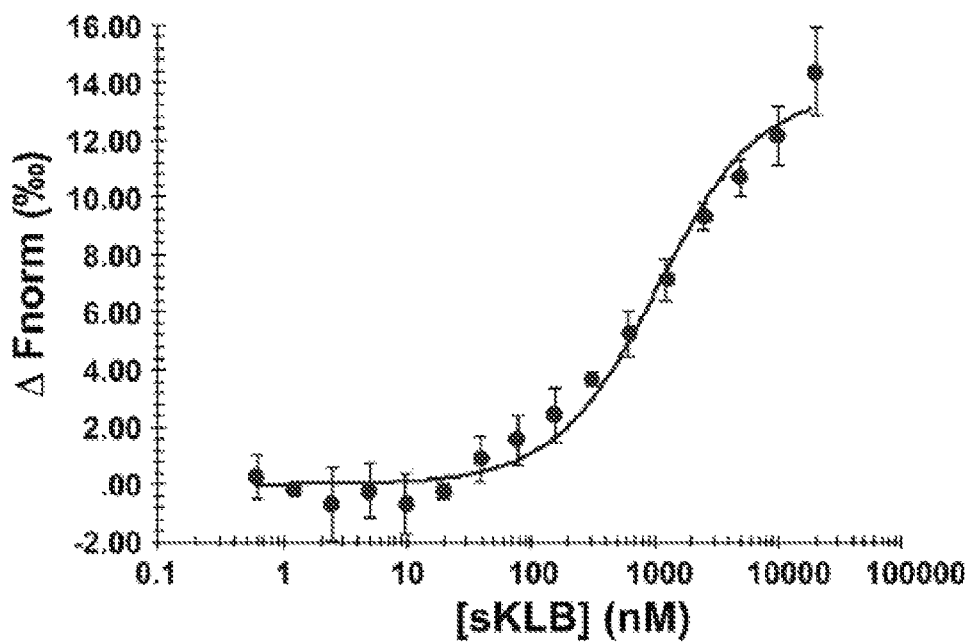
Figure 6C:
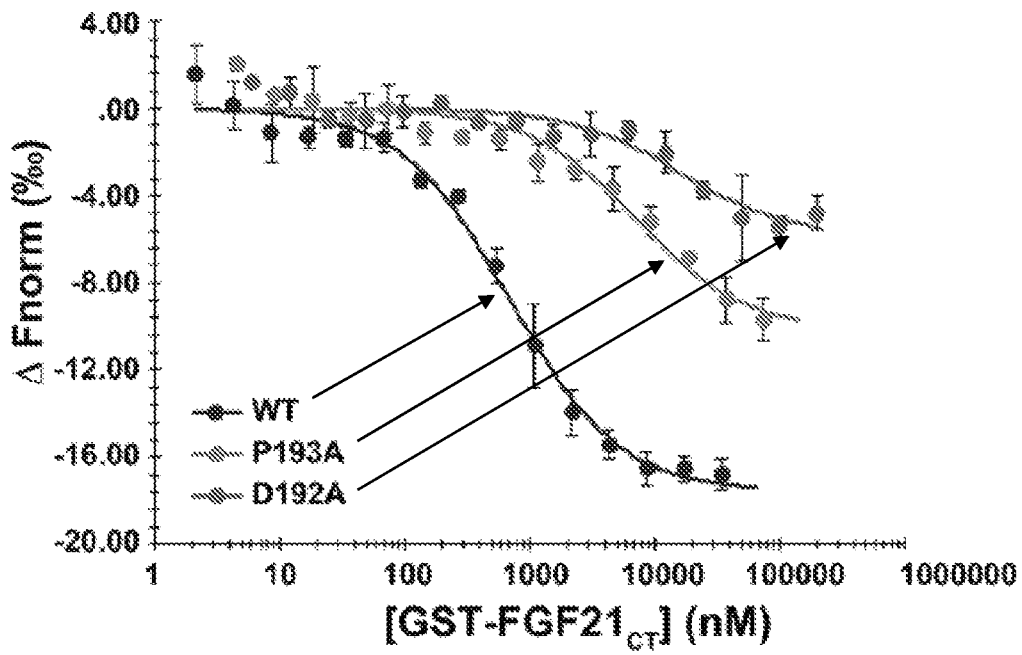

To measure binding of the C-terminal fragment of FGF21 (FGF21$_{CT}$) to sKLB, an MST-based competition assay was used, in which GST-fused FGF21$_{CT}$ (GST-FGF21$_{CT}$) was titrated into a constant sKLB/fl-FGF21 mixture (FIG. 6C). Fitting of the thermophoresis changes arising from competition by GST-FGF21$_{CT}$ using the Hill equation yields an IC$_{50}$ value of 704 nM. SPR-based measurements of sKLB binding to GST-FGF21$_{CT}$ immobilized on a sensor chip using anti-GST also yielded a $K_D$ value of 253 nM, confirming that the C-terminal region of FGF21 is primarily responsible for the high-affinity binding of the ligand to sKLB.

MST was then used to measure the binding affinities of other interactions essential for FGF21-induced stimulation of FGFR1c. MST data obtained using fluorescently labeled FGFR1c$_{D2D3}$ revealed that sKLB binds FGFR1c$_{D2D3}$ with a $K_D$ value of approximately 1 µM (FIG. 6B). By contrast, FGF21 binding to FGFR1c$_{D2D3}$ is too weak for precise $K_D$ determination using MST ($K_D$>10-100 µM) even though the canonical FGF1 binds to the same FGFR1c$_{D2D3}$ protein with $K_D$ of around 1 µM.

Figure 6D:
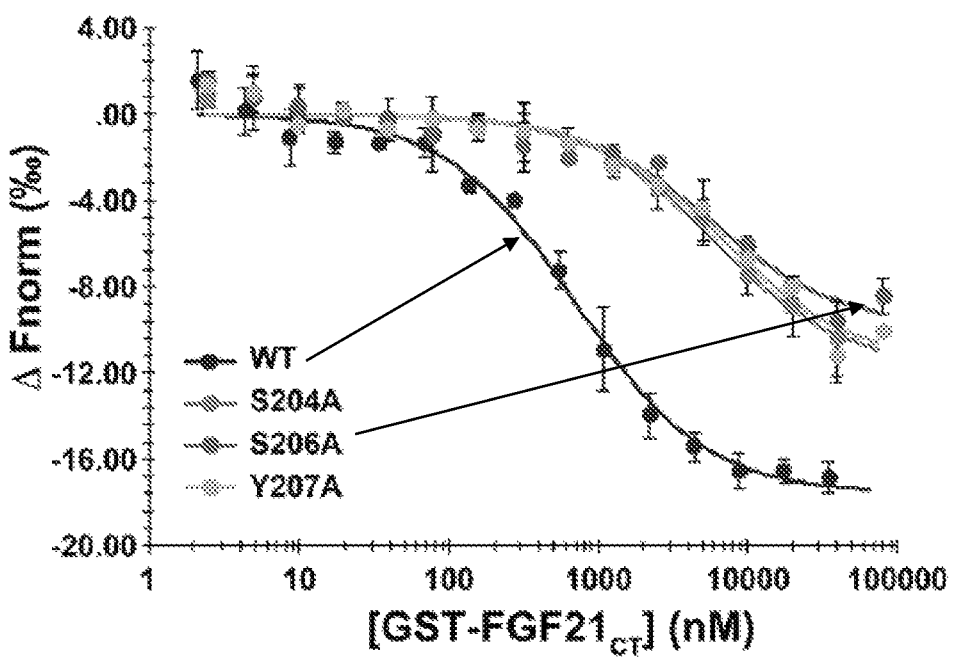

Example 5: β-Klotho Binding Energy is Distributed Along the Length of FGF21$_{CT}$ To determine whether binding of FGF21$_{CT}$ to sKLB is dominated by either the multi-turn element that docks on site 1 (D1) or the pseudosubstrate that binds to site 2 (D2), mutations were generated in both regions and their effects on GST-FGF21$_{CT}$ binding to sKLB were assessed in the MST-based competition assay described elsewhere herein. First, mutations expected to destabilize the internal structure of the multi-turn element in FGF21$_{CT}$ (FIG. 4B) were tested, specifically D192A and P193A mutations that disrupt intramolecular hydrogen bonds that stabilize the D192-P193-L194-S195 0-turn. As anticipated, IC$_{50}$ values measured for D192A or P193A-mutated GSTFGF21$_{CT}$ variants were 10-20 fold higher than those for wild-type (FIG. 6C). Second, mutations that should disrupt central intermolecular interactions between the S—P—S pseudosubstrate region of FGF21$_{CT}$ and site 2 (D2) of β-Klotho (FIG. 5D) were tested. As shown in FIG. 6D, replacing S204 or, S206 or Y207 in GST-FGF21$_{CT}$ with alanines causes an 8-10-fold increase in IC$_{50}$.

These data indicate that binding of FGF21$_{CT}$ to β-Klotho involves both elements in FGF21$_{CT}$, and is mediated by their cooperative binding to both site 1 and site 2 in β-Klotho. Moreover, the results indicate that both site 1 and site 2 must be occupied in order to maintain stable interactions between FGF21$_{CT}$ and β-Klotho. This conclusion is also suggested by the crystal structure. In parallel, SPR and/or MST studies showed that loss of the 10 C-terminal amino acids from FGF21 abolishes its binding to β-Klotho, and that loss of D2 from β-Klotho abolishes its binding to wild-type FGF21. Thus, FGF21 binding to neither site 1 nor site 2 alone is sufficient for stable binding to β-Klotho, indicating that FGF21/β-Klotho complex formation is mediated by cooperation of multiple weak binding events, primarily to site 1 and site 2.

Figure 6E:
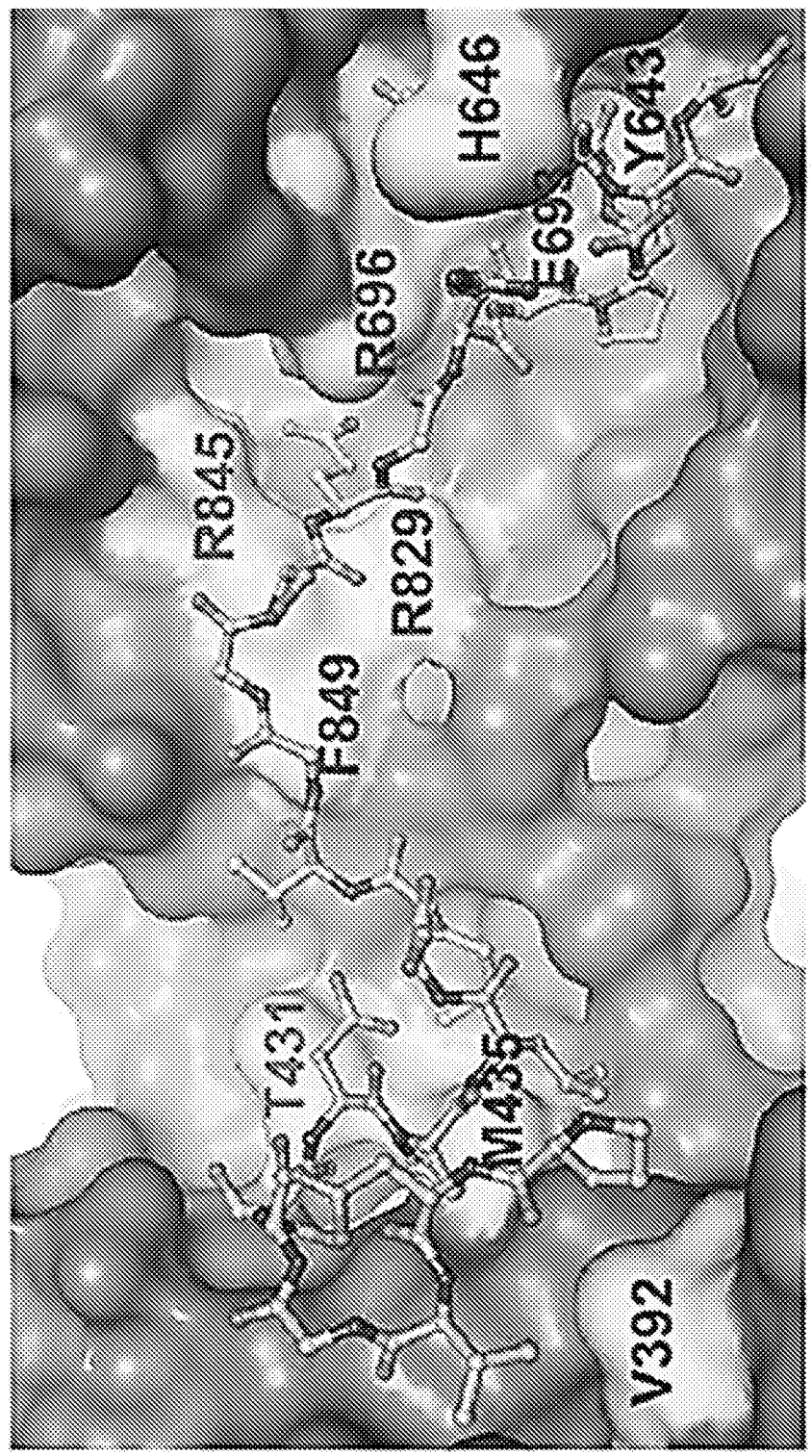
Figure 6F:
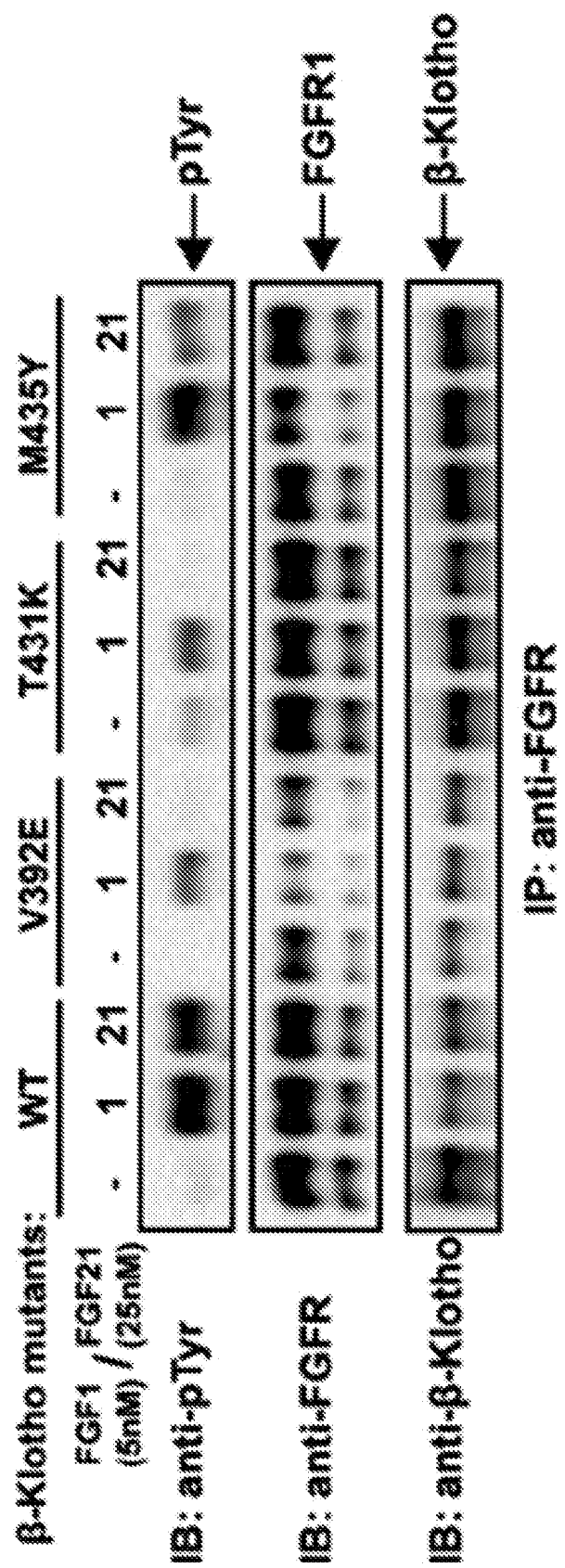
Figure 6G:
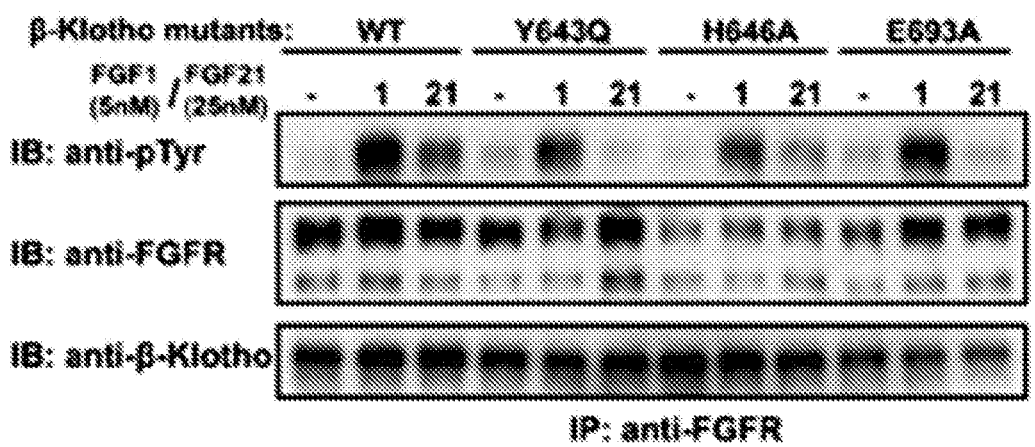
Figure 6G:
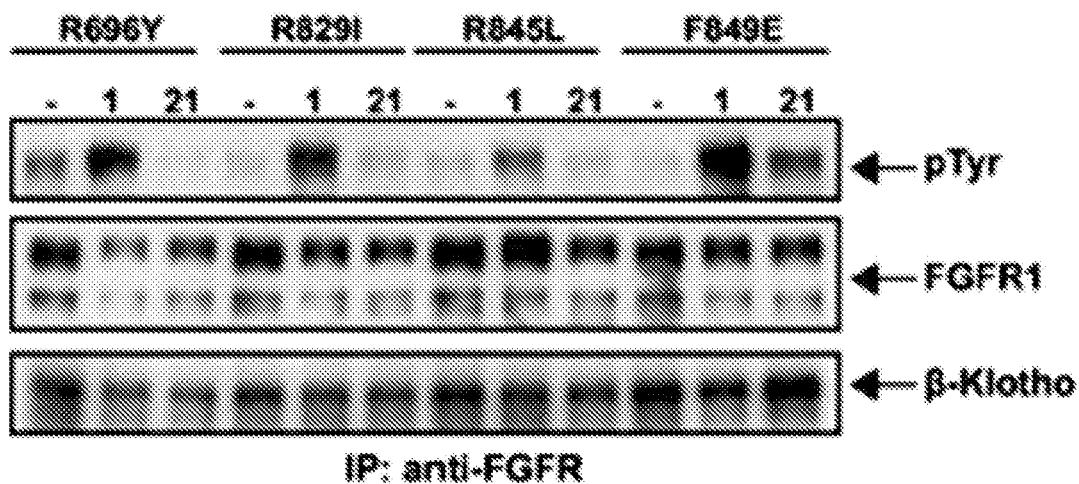

Example 6: Mutating β-Klotho's FGF21-Binding-Interface Impairs Receptor Activation but not Klotho/FGFR1 Interactions Effects of mutations in β-Klotho's two FGF21$_{CT}$-binding sites on the ability of FGF21 to stimulate FGFR1 activation in transfected L6 myoblasts (FIGS. 6E-6G) were investigated. L6 cells lack endogenous FGFRs and β-Klotho, but were engineered to express ectopically either human FGFR1c or β-Klotho alone, or to co-express FGFR1c and β-Klotho (at matched levels). As expected, FGF21 stimulates FGFR1c tyrosine phosphorylation only in cells that co-express FGFR1c and β-Klotho, whereas FGF1 activates FGFR1c to similar levels regardless of β-Klotho's presence. Three independent mutations in site 1 on D1, replacing V392, T431, and M435 individually with their corresponding residues in α-Klotho (which does not bind FGF21), caused a substantial decrease in FGF21 stimulation of FGFR1c (FIG. 6F) tyrosine phosphorylation. Similarly, mutating key amino acids in the pseudo-substrate binding site of D2 or site 2 (Y643, H646, E693, R696, R829 or R845) almost completely abolished FGF21-induced stimulation of FGFR1c, while leaving FGF1-induced stimulation of the receptor unaffected in the same cells (FIG. 6G). Mutating F849, by contrast, which abuts the linker between the two parts of the FGF21$_{CT}$ ligand (FIG. 6E), had relatively little effect (FIG. 6G) on FGF21-induced receptor activation, consistent with the bipartite nature of the interface discussed elsewhere herein. The β-Klotho mutations did not affect interactions between FGFR1c and β-Klotho as assessed by their levels in anti-FGFR1c immunoprecipitates (FIGS. 6F-6G), indicating that FGF21 must activate a pre-existing FGFR1c/β-Klotho complex.

Figure 7A:
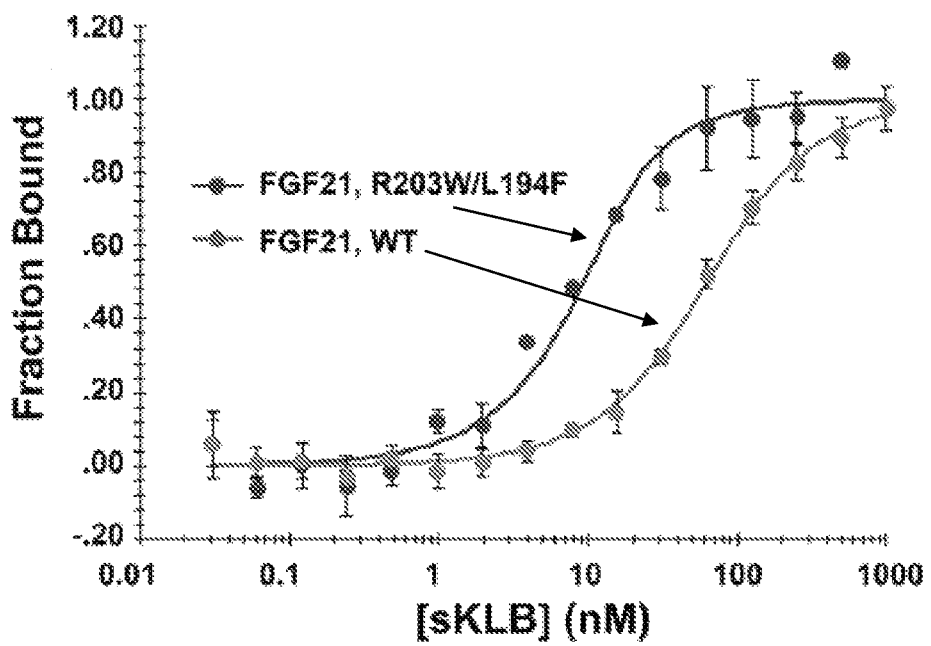
FIGS. 7A-7B illustrate an exemplary structure-based engineering of a superior analogue of FGF21 Enhanced binding affinity (FIG. 7A) and bioactivity (FIG. 7B) of an FGF21 mutant. MST binding measurements of FGF21 carrying a double L194F/R203W mutations in FGF21$_{CT}$ reveal approximately 10-fold increase in binding affinity to sKLB with a $K_D$ of 3.4±1.3 nM and approximately 10-fold enhanced potency for stimulation of FGFR1c tyrosine phosphorylation.
Figure 7B:
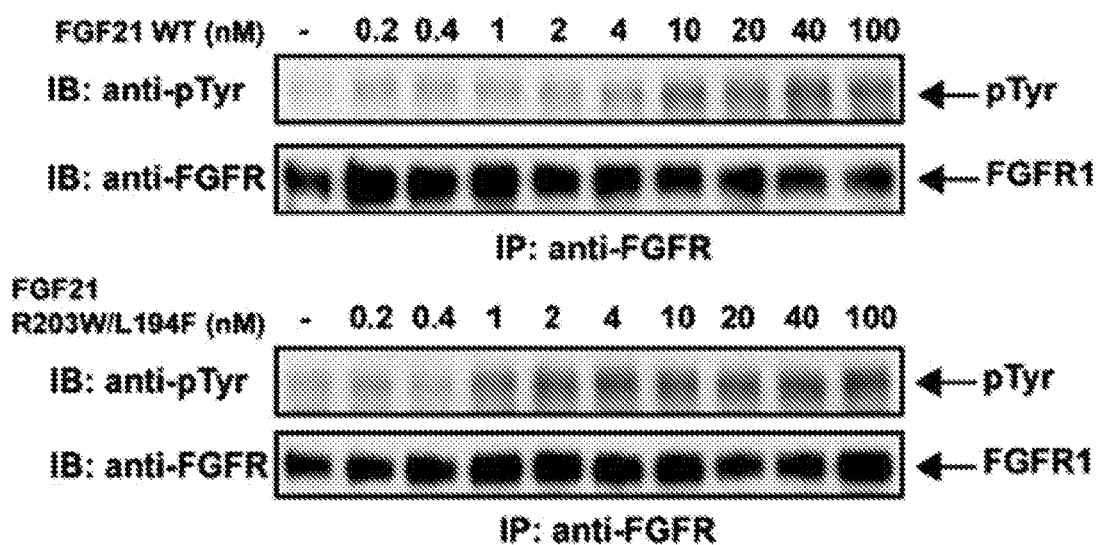
Figure 8:
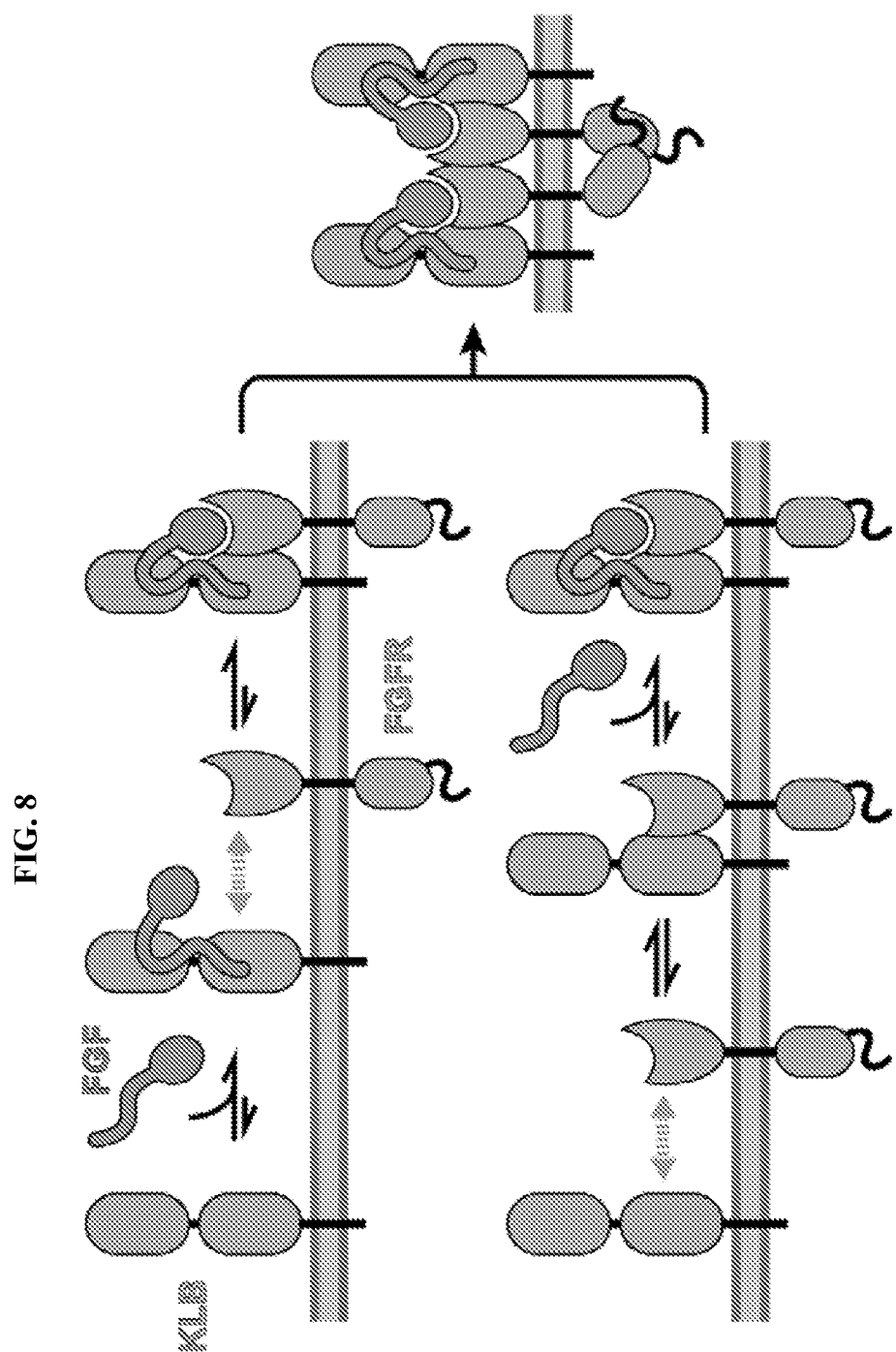
FIG. 8 illustrates an exemplary mechanism of endocrine FGF activation and signaling via complex mediation involving β-Klotho and FGF receptors. In the cell membrane of unstimulated cells, β-Klotho and FGFR1c monomers are in equilibrium with FGFR/β-Klotho heterodimers. Due to reduced dimensionality, the binding of FGF21 to β-Klotho via FGF21 C-tail and bivalent binding of the FGF core of FGF21 to two FGFR1c molecules will shift the equilibrium towards formation of a FGF21/FGFR1c/β-Klotho ternary complexes, resulting in stimulation of tyrosine kinase activity and cell signaling via FGFR1c. In addition, β-Klotho functions as a primary high affinity receptor for FGF21, and FGFR1c functions as a catalytic subunit that mediate receptor dimerization and intracellular signaling.

Example 7: Structure-Guided Engineering of an FGF21 Variant with Improved Binding and Activity As endocrine FGFs play important roles in the control of metabolic processes, a variety of approaches have been utilized to develop novel therapeutics that retain (and exceed in potency) the beneficial stimulatory responses of FGF19 and or FGF21 while minimizing the side effects caused by these two hormones. Inspection of the sKLB/FGF21$_{CT}$ complex structure, together with elucidation of the molecular mechanism of FGF21 activation of the FGFR1c/β-Klotho complex offers new opportunities for structure-guided engineering of novel endocrine FGF analogs with superior hormonal activities. In certain non-limiting embodiments, potency of FGF21 can be enhanced by introducing mutations into its C-terminal tail that strengthen interactions with β-Klotho. An L194F mutation was introduced to increase hydrophobic interactions with neighboring amino acids in site 1 of β-Klotho. R203 in FGF21 was also mutated to tryptophan to replace cation-pi interactions between R203 and H646 with pi-pi interactions on site 2 of β-Klotho. In MST studies, R203W/L194F-mutated FGF21 (FGF21$_{WF}$) bound to sKLB over 10-fold more tightly than wild-type FGF21, with a $K_D$ of 3.4±1.2 nM (FIG. 7A). Moreover, FGF21$_{WF}$ showed a comparably enhanced ability to stimulate FGFR1c autophosphorylation in L6 cells coexpressing β-Klotho and FGFR1c (FIG. 7B).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A soluble FGF21 polypeptide comprising amino acid residues 169-209 of SEQ ID NO:3 (FGF21$_{CT}$),
wherein the polypeptide comprises a mutation in at least one amino acid residue selected from L194 and R203 of SEQ ID NO:3,
further wherein the polypeptide lacks amino acid residues 1-168 of SEQ ID NO:3.

2. The polypeptide of claim 1, wherein the mutation in the at least one amino acid residue is at least one of L194F and R203W of SEQ ID NO:3.

3. The polypeptide of claim 2, wherein the mutation in the at least one amino acid residue is L194F of SEQ ID NO:3.

4. The polypeptide of claim 1, further comprising a peptide selected from the group consisting of albumin, thioredoxin, glutathione S-transferase, and a Fc region of an antibody.

5. The polypeptide of claim 4, wherein the peptide comprises the Fc region of an antibody, and wherein the Fc region is linked to the soluble FGF21 polypeptide through a polypeptide comprising about 1-18 amino acids.

* * * * *